US012357755B2

(12) United States Patent
Fanning et al.

(10) Patent No.: US 12,357,755 B2
(45) Date of Patent: Jul. 15, 2025

(54) FLUID MANAGEMENT SYSTEM AND METHOD FOR CONTROLLING INTRACAVITY PRESSURE

(71) Applicant: BOSTON SCIENTIFIC SCIMED, INC., Maple Grove, MN (US)

(72) Inventors: Leah Fanning, Clonmel (IE); Paul Byrne, Kilkenny (IE); Niraj Prasad Rauniyar, Plymouth, MN (US); Evan Gyllenhaal, Sudbury, MA (US); Vivek Shah, Reading, MA (US); Nishant Khattar, White Bear Township, MN (US); Noel Smith, County Kilkenny (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1245 days.

(21) Appl. No.: 17/125,009

(22) Filed: Dec. 17, 2020

(65) Prior Publication Data

US 2021/0236728 A1 Aug. 5, 2021

Related U.S. Application Data

(60) Provisional application No. 62/967,806, filed on Jan. 30, 2020.

(51) Int. Cl.
*A61M 5/172* (2006.01)
*A61M 5/142* (2006.01)
(Continued)

(52) U.S. Cl.
CPC .......... *A61M 5/1723* (2013.01); *A61M 5/142* (2013.01); *A61B 1/015* (2013.01);
(Continued)

(58) Field of Classification Search
CPC .............. A61M 5/1723; A61M 5/142; A61M 2205/3331; A61M 2205/3334;
(Continued)

(56) References Cited

U.S. PATENT DOCUMENTS

| 4,526,574 A | 7/1985 | Pekkarinen |
| 4,650,462 A | 3/1987 | Desatnick et al. |

(Continued)

FOREIGN PATENT DOCUMENTS

| CN | 1200741 C | 5/2005 |
| EP | 0329599 A1 | 8/1989 |

(Continued)

OTHER PUBLICATIONS

International Search Report and Written Opinion dated Apr. 8, 2021 for International Application No. PCT/US2020/065568.

*Primary Examiner* — Jason E Flick
(74) *Attorney, Agent, or Firm* — Seager, Tufte & Wickhem, LLP

(57) ABSTRACT

A fluid management system may include an inflow pump configured to pump fluid from a fluid supply source to a treatment site within a patient at a flow rate; and a controller configured to operate at a target flow rate in a flow control mode. In the flow control mode, the controller may be configured to maintain the target flow rate while monitoring a measured pressure communicated to the controller from a pressure sensor. When the measured pressure reaches a preset pressure threshold, the controller may be configured to automatically switch from the flow control mode to a pressure override mode in which the controller automatically reduces the flow rate below the target flow rate to return the measured pressure at or below the preset pressure threshold.

20 Claims, 14 Drawing Sheets

(51) Int. Cl.
*A61B 1/015* (2006.01)
*A61M 3/02* (2006.01)

(52) U.S. Cl.
CPC .......... *A61M 3/0216* (2014.02); *A61M 3/022* (2014.02); *A61M 2205/3331* (2013.01); *A61M 2205/3334* (2013.01); *A61M 2205/502* (2013.01); *A61M 2205/583* (2013.01)

(58) Field of Classification Search
CPC ...... A61M 2205/502; A61M 2205/583; A61M 2205/3344; A61M 2205/505; A61M 3/022; A61M 3/0216; A61M 5/14; A61M 5/168; A61M 5/172; A61M 2005/1726; A61M 2005/14208; A61M 2205/33; A61B 1/015
See application file for complete search history.

(56) References Cited

U.S. PATENT DOCUMENTS

| | | |
|---|---|---|
| 4,998,914 A | 3/1991 | Wiest et al. |
| 5,460,490 A | 10/1995 | Carr et al. |
| 5,464,391 A | 11/1995 | Devale |
| 5,630,798 A | 5/1997 | Beiser et al. |
| 5,685,821 A | 11/1997 | Pike |
| 5,709,670 A | 1/1998 | Vancaille et al. |
| 5,800,383 A | 9/1998 | Chandler et al. |
| 5,803,917 A * | 9/1998 | Butterfield ........ A61M 5/16859 604/67 |
| 5,810,770 A | 9/1998 | Chin et al. |
| 5,830,180 A | 11/1998 | Chandler et al. |
| 5,882,339 A | 3/1999 | Beiser et al. |
| 6,024,720 A | 2/2000 | Chandler et al. |
| 6,077,246 A | 6/2000 | Kullas et al. |
| 6,159,160 A | 12/2000 | Hsei et al. |
| 6,595,957 B1 | 7/2003 | Griffiths et al. |
| 6,896,664 B2 | 5/2005 | Novak |
| 7,083,601 B1 | 8/2006 | Cosmescu |
| 7,604,610 B2 | 10/2009 | Shener et al. |
| 7,981,073 B2 | 7/2011 | Möllstam et al. |
| D657,865 S | 4/2012 | Williams |
| 8,444,592 B2 | 5/2013 | Williams et al. |
| 8,512,326 B2 | 8/2013 | Shadduck et al. |
| 8,597,228 B2 | 12/2013 | Pyles et al. |
| 8,728,066 B2 | 5/2014 | Shadduck et al. |
| 8,790,303 B2 | 7/2014 | Williams et al. |
| 8,795,232 B2 | 8/2014 | Visconti et al. |
| 8,974,448 B2 | 3/2015 | Germain et al. |
| 9,084,847 B2 | 7/2015 | Klein et al. |
| 9,233,193 B2 | 1/2016 | Truckai et al. |
| 9,247,983 B2 | 2/2016 | Truckai et al. |
| 9,254,142 B2 | 2/2016 | Germain et al. |
| 9,272,086 B2 | 3/2016 | Williams et al. |
| 9,289,110 B2 | 3/2016 | Woolford et al. |
| 9,322,729 B2 | 4/2016 | Heide et al. |
| 9,439,677 B2 | 9/2016 | Germain et al. |
| 9,439,720 B2 | 9/2016 | Germain et al. |
| 9,474,848 B2 | 10/2016 | Williams et al. |
| 9,486,233 B2 | 11/2016 | Bek et al. |
| 9,498,244 B2 | 11/2016 | Orczy-Timko et al. |
| 9,549,754 B2 | 1/2017 | Shadduck et al. |
| 9,597,149 B2 | 3/2017 | Germain et al. |
| 9,603,990 B2 | 3/2017 | Woolford |
| 9,636,170 B2 | 5/2017 | Germain et al. |
| 9,737,362 B2 | 8/2017 | Germain et al. |
| 9,743,979 B2 | 8/2017 | Germain et al. |
| 9,770,541 B2 | 9/2017 | Carr et al. |
| 9,827,037 B2 | 11/2017 | Germain et al. |
| 9,839,473 B2 | 12/2017 | Germain et al. |
| 9,889,246 B2 | 2/2018 | Woolford |
| 9,901,665 B2 | 2/2018 | Klein et al. |
| 9,907,563 B2 | 3/2018 | Germain et al. |
| 9,943,639 B2 | 4/2018 | Germain et al. |
| 9,999,466 B2 | 6/2018 | Germain et al. |
| 10,004,556 B2 | 6/2018 | Orczy-Timko et al. |
| 10,178,942 B2 | 1/2019 | Germain et al. |
| 10,238,412 B2 | 3/2019 | Bek et al. |
| 10,349,815 B2 | 7/2019 | Germain et al. |
| 10,368,912 B2 | 8/2019 | Truckai et al. |
| 10,441,353 B2 | 10/2019 | Germain et al. |
| 10,499,987 B2 | 12/2019 | Germain et al. |
| 10,518,005 B2 | 12/2019 | Carr et al. |
| 10,531,785 B2 | 1/2020 | Germain et al. |
| 10,531,912 B2 | 1/2020 | Germain et al. |
| 10,603,104 B2 | 3/2020 | Germain et al. |
| 10,667,857 B2 | 6/2020 | Shadduck et al. |
| 10,716,584 B2 | 7/2020 | Germain et al. |
| 10,751,451 B2 | 8/2020 | Klein et al. |
| 10,786,619 B2 | 9/2020 | Germain et al. |
| 2008/0154095 A1 | 6/2008 | Stubkjaer et al. |
| 2012/0191037 A1 | 7/2012 | Patel et al. |
| 2012/0283691 A1 * | 11/2012 | Barnes .................... A61M 5/00 604/67 |
| 2013/0197471 A1 | 8/2013 | Williams et al. |
| 2013/0245599 A1 | 9/2013 | Williams et al. |
| 2013/0253498 A1 | 9/2013 | Germain et al. |
| 2014/0336599 A1 | 11/2014 | Patel et al. |
| 2015/0290404 A1 | 10/2015 | Torisawa et al. |
| 2015/0328379 A1 | 11/2015 | Carr et al. |
| 2017/0000957 A1 | 1/2017 | Carr et al. |
| 2017/0027637 A1 | 2/2017 | Germain et al. |
| 2017/0056102 A1 | 3/2017 | Germain et al. |
| 2017/0203028 A1 | 7/2017 | Carr et al. |
| 2018/0000998 A1 | 1/2018 | Carr et al. |
| 2018/0132930 A1 | 5/2018 | Germain et al. |
| 2018/0168667 A1 * | 6/2018 | Germain ................ A61B 17/22 |
| 2018/0207332 A1 | 7/2018 | Reever et al. |
| 2018/0271596 A1 | 9/2018 | Germain et al. |
| 2018/0361055 A1 | 12/2018 | Pereira et al. |
| 2019/0175204 A1 | 6/2019 | Bek et al. |
| 2019/0321096 A1 | 10/2019 | Germain et al. |
| 2019/0336166 A1 | 11/2019 | Truckai et al. |
| 2020/0100836 A1 | 4/2020 | Germain et al. |
| 2020/0121387 A1 | 4/2020 | Germain et al. |
| 2020/0246067 A1 | 8/2020 | Germain et al. |
| 2020/0281645 A1 | 9/2020 | Shadduck et al. |
| 2020/0315640 A1 | 10/2020 | Germain et al. |

FOREIGN PATENT DOCUMENTS

| | | |
|---|---|---|
| FR | 2727847 A1 | 6/1996 |
| JP | H07178044 A | 7/1995 |

* cited by examiner

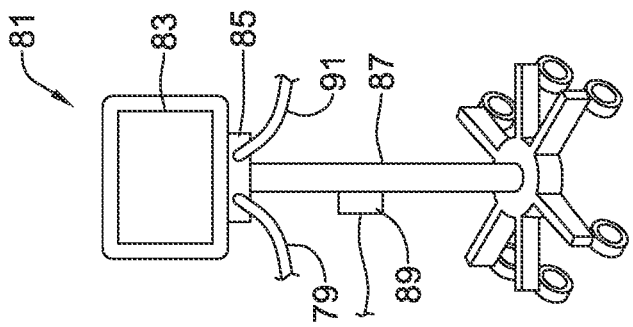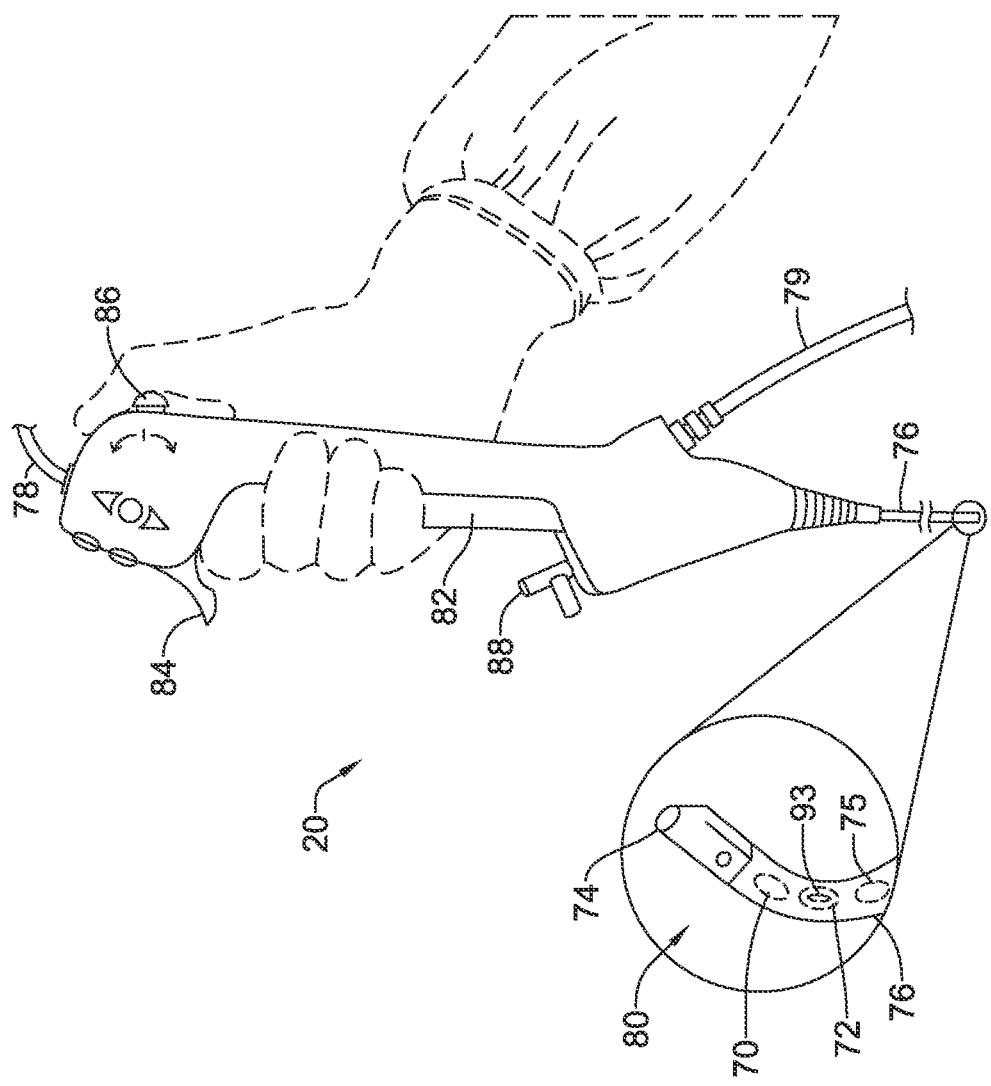
FIG. 2

FLUID MANAGEMENT SYSTEM AND METHOD FOR CONTROLLING INTRACAVITY PRESSURE

CROSS REFERENCE TO RELATED APPLICATIONS

The present application claims the benefit of and priority to U.S. Provisional Patent Application Ser. No. 62/967,806, filed on Jan. 30, 2020, the disclosure of which is incorporated herein by reference.

TECHNICAL FIELD

The disclosure is directed to a fluid management system. More particularly, the disclosure is directed to a fluid management system and method for controlling intracavity pressure.

BACKGROUND

Flexible ureteroscopy (fURS), gynecology, and other endoscopic procedures require the circulation of fluid for several reasons. Surgeons today deliver the fluid in various ways such as, for example, by hanging a fluid bag and using gravity to deliver the fluid, filling a syringe and manually injecting the fluid, or using a peristaltic pump to deliver fluid from a reservoir at a fixed pressure or flow rate via a fluid management system. Fluid management systems may adjust the flow rate and/or pressure at which fluid is delivered from the reservoir based on data collected from a procedural device, such as, but not limited to, an endoscope and/or the fluid management system. Of the known medical devices, systems, and methods, each has certain advantages and disadvantages. There is an ongoing need to provide alternative medical devices and fluid delivery systems.

SUMMARY

In one example, a fluid management system may comprise an inflow pump configured to pump fluid from a fluid supply source to a treatment site within a patient at a flow rate; and a controller configured to operate at a target flow rate in a flow control mode. In the flow control mode, the controller may be configured to maintain the target flow rate while monitoring a measured pressure communicated to the controller from a pressure sensor. When the measured pressure reaches a preset pressure threshold, the controller may be configured to automatically switch from the flow control mode to a pressure override mode in which the controller automatically reduces the flow rate below the target flow rate to return the measured pressure at or below the preset pressure threshold.

In addition or alternatively to any example disclosed herein, the controller is configured to switch from the pressure override mode back to the flow control mode when the measured pressure falls below the preset pressure threshold.

In addition or alternatively to any example disclosed herein, the controller is configured to display a prompt on a display asking if a user wants to switch back to the flow control mode when the measured pressure falls below the preset pressure threshold.

In addition or alternatively to any example disclosed herein, the controller is configured to display a notification on a display and automatically switch from the pressure override mode back to the flow control mode when the measured pressure falls below the preset pressure threshold.

In addition or alternatively to any example disclosed herein, the controller is configured to switch from the pressure override mode to an adjusted flow control mode when the measured pressure falls below the preset pressure threshold.

In addition or alternatively to any example disclosed herein, the controller is configured to operate at the reduced flow rate of the pressure override mode when in the adjusted flow control mode.

In addition or alternatively to any example disclosed herein, the controller is configured to display a prompt on a display asking if a user wants to switch to the adjusted flow control mode when the measured pressure falls below the preset pressure threshold.

In addition or alternatively to any example disclosed herein, the controller is configured to display a notification on a display and automatically switch from the pressure override mode to the adjusted flow control mode when the measured pressure falls below the preset pressure threshold.

In addition or alternatively to any example disclosed herein, the measured pressure is an intracavity pressure measured within the treatment site.

In addition or alternatively to any example disclosed herein, the preset pressure threshold is an intracavity pressure limit.

In addition or alternatively to any example disclosed herein, the measured pressure is a system pressure measured within the fluid management system.

In addition or alternatively to any example disclosed herein, the preset pressure threshold is a system pressure limit.

In addition or alternatively to any example disclosed herein, a fluid management system may comprise an inflow pump configured to pump fluid from a fluid supply source to a treatment site within a patient at a flow rate; and a controller configured to operate at a target flow rate in a flow control mode. In the flow control mode, the controller may be configured to maintain the target flow rate while monitoring a measured pressure communicated to the controller from a pressure sensor. When the measured pressure reaches a preset pressure threshold, the controller may be configured to automatically switch from the flow control mode to a pressure override mode in which the controller automatically reduces the flow rate below the target flow rate to return the measured pressure at or below the preset pressure threshold. The controller may be configured to display a prompt on a display asking if a user wants to switch out of the pressure override mode when the measured pressure falls below the preset pressure threshold.

In addition or alternatively to any example disclosed herein, the controller is configured to switch from the pressure override mode back to the flow control mode when the measured pressure falls below the preset pressure threshold.

In addition or alternatively to any example disclosed herein, the controller is configured to switch from the pressure override mode to an adjusted flow control mode when the measured pressure falls below the preset pressure threshold.

In addition or alternatively to any example disclosed herein, in the adjusted flow control mode, the flow rate is thereafter maintained at the reduced flow rate associated with the pressure override mode.

In addition or alternatively to any example disclosed herein, the prompt asks if the user wants to switch back to the flow control mode or to an adjusted flow control mode.

In addition or alternatively to any example disclosed herein, a method of controlling fluid flow in a fluid management system, wherein the fluid management system comprises an inflow pump configured to pump fluid from a fluid supply source to a treatment site within a patient at a flow rate and a controller configured to operate at a target flow rate in a flow control mode, the method comprising: setting parameters within the controller, wherein the parameters include the target flow rate and a preset pressure threshold; operating the controller in the flow control mode, wherein the controller maintains the target flow rate while monitoring a measured pressure communicated to the controller from a pressure sensor; when the measured pressure reaches the preset pressure threshold, automatically switching the controller from the flow control mode to a pressure override mode in which the controller automatically reduces the flow rate below the target flow rate to return the measured pressure at or below the preset pressure threshold; and displaying a prompt on a display asking if a user wants to switch out of the pressure override mode when the measured pressure falls below the preset pressure threshold.

In addition or alternatively to any example disclosed herein, the preset pressure threshold is an intracavity pressure limit.

In addition or alternatively to any example disclosed herein, the preset pressure threshold is a system pressure limit.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The invention may be more completely understood in consideration of the following detailed description in connection with the accompanying drawings, in which:

FIG. 2 illustrates selected aspects of a medical device and a workstation of the system of FIG. 1;

Figure 1:
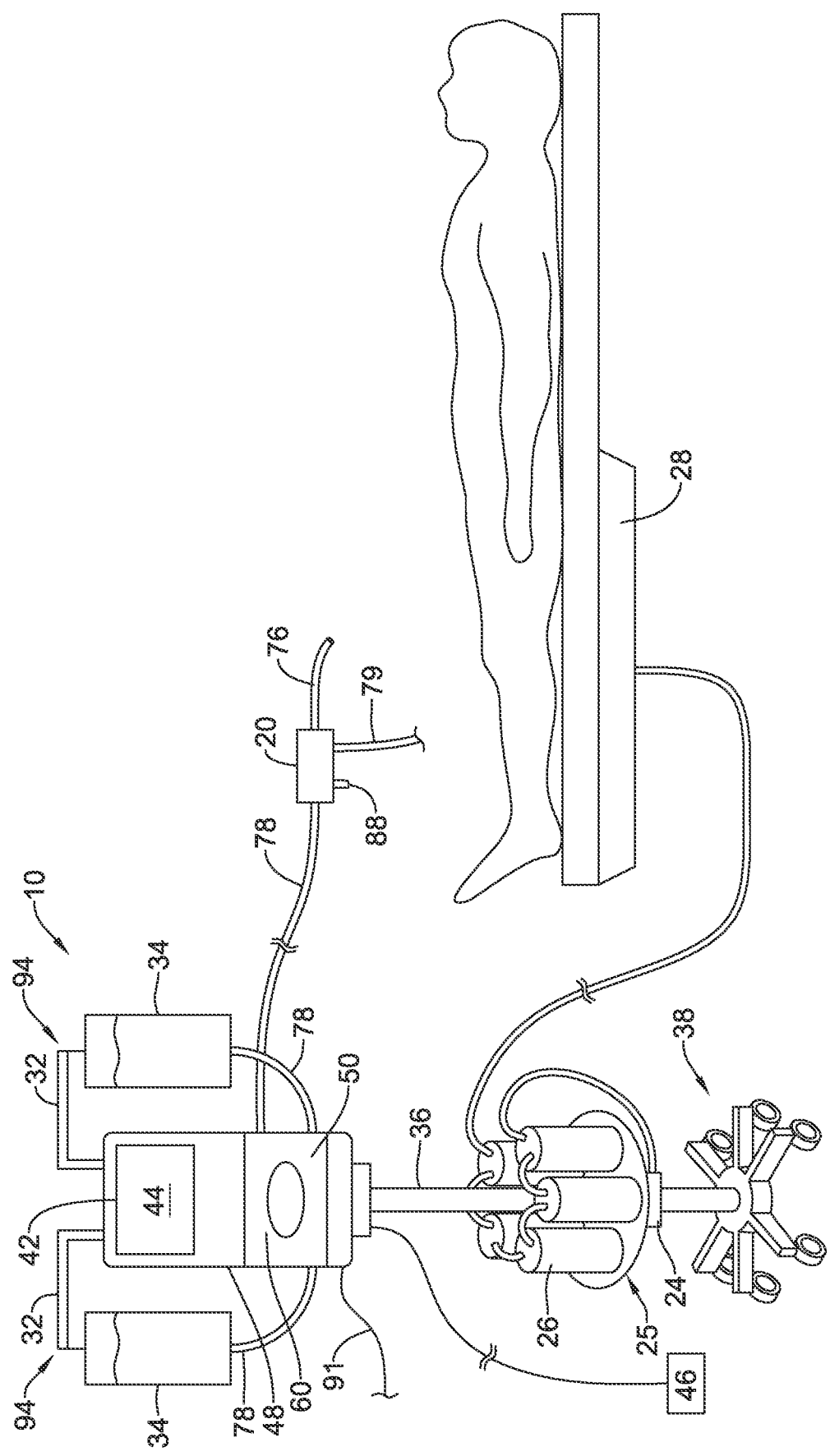
FIG. 1 is a schematic illustration of selected aspects of a fluid management system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some fluid management systems for use in flexible ureteroscopy (fURS) procedures (e.g., ureteroscopy, percutaneous nephrolithotomy (PCNL), benign prostatic hyperplasia (BPH), transurethral resection of the prostate (TURP), etc.), gynecology, and other endoscopic procedures may regulate body cavity pressure when used in conjunction with an endoscope device, such as but not limited to a LithoVue™ scope device, using pressure and/or temperature data from the endoscope or other endoscopic device. During fURS procedures, the body cavity may be distended to make it easier to locate a target. In some procedures, blood and/or debris may be present in the body cavity, which may affect negatively image quality through the endoscopic device. Fluid flow (e.g., irrigation) through the endoscopic device may be used to flush the body cavity to improve image quality. In some procedures, the body cavity may be relatively small and irrigation fluid may flow continuously, which can raise intracavity fluid pressure and/or system pressure (e.g., fluid pressure within the fluid management system itself). Increased intracavity fluid pressure and/or system pressure may pose risks to the patient under some circumstances. As such, there is a need to maintain fluid flow (e.g., irrigation) into the body cavity to maintain good visualization while limiting and/or reducing intracavity fluid pressure and/or system pressure.

FIG. 1 is a schematic view of a fluid management system 10 that may be used in an endoscopic procedure, such as fURS procedures. The fluid management system 10 may be coupled to a medical device 20 that allows flow of fluid therethrough. In some embodiments, the fluid management system 10 and/or the medical device 20 may include a pressure sensor. In some embodiments, the medical device 20 may be a LithoVue™ scope device, or other endoscope. In an illustrative embodiment, the medical device 20 may include a temperature sensor to provide intracavity temperature feedback to the fluid management system 10, a pressure sensor to provide intracavity pressure feedback to the fluid management system 10, and/or a camera to provide visual feedback to the fluid management system 10. Some specific and/or additional features of the fluid management system 10 and/or the medical device 20 shown in FIG. 1 may not be specifically referenced with respect to FIG. 1, but will be discussed below and/or in conjunction with other figures. Such features are shown in FIG. 1 for context.

Briefly, the fluid management system 10 may include an inflow pump 50 configured to pump and/or transfer fluid from a fluid supply source 34 (e.g., a fluid bag, etc.) to the medical device 20 and/or a treatment site within a patient at a fluid flow rate. In some cases, the fluid may pass through a fluid warming system 60 prior to entering the medical device 20. The flow of fluid, the pressure of the fluid, the temperature of the fluid, and/or other operational parameters may be controlled by or at least partially controlled by a controller 48. The controller 48 may be in electronic communication (e.g., wired or wireless) with the medical device 20, the inflow pump 50, and/or the fluid warming system 60 to provide control commands and/or to transfer or receive data therebetween. For example, the controller 48 may receive data from the medical device 20 such as, but not limited to, pressure and temperature data. The controller 48 may then use the data received from the medical device 20 to control operational parameters of the inflow pump 50 and/or the fluid warming system 60.

In some embodiments, the controller 48 may be configured to operate at a target fluid flow rate in a flow control mode. In some embodiments, in the flow control mode, the controller 48 may be configured to control the inflow pump 50 to maintain the target fluid flow rate based on a set of system operating parameters while monitoring a measured pressure communicated to the controller 48 from a pressure sensor. In some embodiments, when the measured pressure reaches a preset pressure threshold, the controller 48 may be configured to automatically switch from the flow control mode to a pressure override mode in which the controller 48 automatically reduces the fluid flow rate below the target fluid flow rate to return the measured pressure at or below the preset pressure threshold. In some embodiments, the controller 48 may be configured to control the inflow pump 50 to maintain a desired intracavity fluid pressure at the treatment site and/or a target flow rate based on a set of system operating parameters.

The fluid management system 10 also includes a fluid management unit. An illustrative fluid management unit may include one or more fluid container supports, such as fluid supply source hanger(s) 32, each of which supports one or more fluid supply sources 34 (e.g., one or more fluid bags). In some embodiments, placement and/or weight of the fluid supply source 34 (e.g., the fluid bag) may be detected using a remote sensor and/or a supply load cell 94 associated with and/or operatively coupled to each fluid supply source hanger 32 and/or fluid container support. The controller 48 may be in electronic communication with the supply load cell 94. The fluid supply source hanger(s) 32 may receive a variety of sizes of fluid supply sources 34 such as, for example, 1 liter (L) to 5 L fluid supply sources (e.g., fluid bags). It will be understood that any number of fluid supply sources 34 may be used. Furthermore, fluid supply sources 34 of any size may be used depending on the procedure. In some embodiments, the fluid management unit may be mounted to a rolling stand, which may include a pole 36 and/or a base 38. The base 38 may include a plurality of wheels to facilitate easy movement of the fluid management unit when in use. However, it will be understood that the fluid supply source 34 may also be hung from the ceiling or other location depending on the clinical preference. The fluid supply source hanger(s) 32 may extend from the pole 36 and/or the controller 48 and may include one or more hooks from which one or more fluid supply sources 34 may be suspended. In some embodiments, the fluid used in the fluid management unit may be 0.9% saline. However, it will be understood that a variety of other fluids of varying viscosities may be used depending on the procedure.

In some embodiments, the fluid management unit may include a vacuum pump 24 and a collection container 26 in fluid communication with a collection drape 28. In some embodiments, the vacuum pump 24 may include a plurality of vacuum pumps. In some embodiments, the collection container 26 may include a plurality of containers, canisters, and/or other receptacles, which may be fluidly connected to each other and/or the vacuum pump 24. In some embodiments, the collection drape 28 may include a plurality of collection drapes. The vacuum pump 24 may be operatively and/or electronically connected to the controller 48. In some embodiments, the vacuum pump 24 may be disposed adjacent to and/or near the collection container 26, as illustrated in FIG. 1. In some embodiments, the vacuum pump 24 may be disposed within the fluid management system 10. Other configurations are also contemplated. In some embodiments, the collection container 26 may be operatively coupled to a collection load cell 25 to detect placement and/or weight of the collection container 26. In embodiments having a plurality of containers, canisters, and/or other receptacles, each container, canister, and/or receptacle may be operatively coupled to a corresponding collection load cell 25. The controller 48 may be in electronic communication with the collection load cell(s) 25.

The fluid management system 10 may also include one or more user interface components such as a touch screen interface 42. The touch screen interface 42 includes a display 44 and may include switches or knobs in addition to touch capabilities. In some embodiments, the controller 48 may include the touch screen interface 42 and/or the display 44. The touch screen interface 42 allows the user to input/adjust various functions of the fluid management system 10 such as, for example flow rate, pressure, or temperature. The user may also configure parameters and alarms (such as, but not limited to, an intracavity pressure limit, a system pressure limit, etc.), information to be displayed, and the procedure mode. The touch screen interface 42 allows the user to add, change, and/or discontinue the use of various modular systems within the fluid management system 10. The touch screen interface 42 may also be used to change the fluid management system 10 between automatic and manual modes for various procedures. It is contemplated that other systems configured to receive user input may be used in place of or in addition to the touch screen interface 42.

The touch screen interface 42 may be configured to include selectable areas like buttons and/or may provide a functionality similar to physical buttons as would be understood by those skilled in the art. The display 44 may be configured to show icons related to modular systems and devices included in the fluid management system 10. The display 44 may also include a flow rate display. The flow rate display may be determined based on a desired threshold for flow rate set by the user prior to the procedure or based on known common values, etc. In some embodiments, the operating parameters may be adjusted by touching the corresponding portion of the touch screen interface 42. The touch screen interface 42 may also display visual alerts and/or audio alarms if parameters (e.g., flow rate, pressure, temperature, etc.) are above or below predetermined thresholds and/or ranges. The touch screen interface 42 may also be configured to display the amount of fluid remaining in the fluid supply source 34, and/or any other information the user may find useful during the procedure. In some embodiments, the fluid management system 10 may also include further user interface components such as an optional foot pedal 46, a heater user interface, a fluid control interface, or other device to manually control various modular systems. For example, the optional foot pedal 46 may be used to manually control flow rate. Some illustrative displays and other user interface components are described in described in commonly assigned U.S. Patent Application Publication No. 2018/0361055, titled AUTOMATED FLUID MANAGEMENT SYSTEM, the entire disclosure of which is hereby incorporated by reference.

The touch screen interface 42 may be operatively connected to or may be a part of the controller 48. The controller 48 may be a computer, tablet computer, or other processing device. The controller 48 may be operatively connected to one or more system components such as, for example, the inflow pump 50, the fluid warming system 60, a fluid deficit management system, etc. In some embodiments, these features may be integrated into a single unit. The controller 48 is capable of and configured to perform various functions such as calculation, control, computation, display, etc. The controller 48 is also capable of tracking and storing data pertaining to the operations of the fluid management system 10 and each component thereof. In an illustrative embodiment, the controller 48 includes wired and/or wireless network communication capabilities, such as ethernet or Wi-Fi, through which the controller 48 may be connected to, for example, a local area network. The controller 48 may also receive signals from one or more of the sensors of the fluid management system 10. In some embodiments, the controller 48 may communicate with databases for best practice suggestions and the maintenance of patient records which may be displayed to the user on the display 44.

The fluid management system 10 may be user selectable between different modes based on the procedure, patient characteristics, etc. For example, different modes may include, but are not limited to, Limit mode, Notification mode, etc. Once a mode has been selected by the user, selected system parameters such as target fluid flow rate, intracavity fluid pressure limit, system fluid pressure limit, fluid deficit, and/or temperature may be provided to and/or input by the user via the touch screen interface 42 and/or the display 44. The exemplary parameters of the specific modes may be previously determined and loaded onto the controller 48 using, for example, software. Thus, when a user selects a procedure from an initial display on the display 44 of the touch screen interface 42, these known parameters may be loaded from the controller 48 to the various components of the fluid management system 10, such as, but not limited to the inflow pump 50, the fluid warming system 60, the fluid deficit management system, etc. The fluid management system 10 may also be user selectable between automatic and manual control. For example, for certain procedures, the user may wish to manually adjust a fluid flow rate, fluid pressure, and/or other parameters. Once the user has selected the manual control on, for example, the touch screen interface 42, the user may the adjust fluid flow rate or fluid pressure via other manual interfaces such as the optional foot pedal 46, for example. If the user selects an automatic control, the user may be prompted to select or input via the touch screen interface 42 which medical device 20 is being used so that the controller 48 may determine which data and/or parameters to use to facilitate control of the fluid management system 10. In some embodiments, the fluid management system 10 may be configured to verify the medical device 20 selected is actually being used.

In some embodiments, the fluid management system 10 may include visual software or image recognition and analysis software. For example, the medical device 20 may include a camera 70 (e.g., FIGS. 2 and 4). In some embodiments, the controller 48 may be configured to include visual software/image recognition software that can detect visual noise based on variations in brightness (e.g., light monitoring), contrast, or color pixilation. If the image provided to the controller 48 is determined to be not sufficiently clear or sharp, the fluid management system 10 may temporarily increase the fluid flow rate or the fluid pressure to flush out debris from the treatment site to sharpen/clear the image. The fluid flow rate or the fluid pressure may be manually or automatically increased for a temporary time (e.g., a predetermined time period) or until the field of view is deemed to be sufficiently clear. This temporary increase ensures that the time at which the fluid flow rate or the fluid pressure is increased is limited to ensure that intracavity pressure does not exceed safe limits.

For example, the fluid management system 10 may recognize a red hue in the irrigation (a sign of blood) and signal to the inflow pump 50 to increase the fluid flow rate above the target fluid flow rate until the blood is cleared from the field of view. Alternatively, the controller 48 may provide a visual alert on the display 44 or an audible alert to the physician or nurse that a cloudy view has been detected and the user may then adjust the fluid flow rate manually. In another example, in instances where there is a significant amount of debris, light reflected from the debris may brighten the image substantially. In this situation, the controller 48 detects this inordinate brightness and signals to the inflow pump 50 to increase the fluid flow rate to flush away and/or remove debris. Once the reflected light has been reduced as the debris is flushed clear of the field of view of the vision system, the inflow pump 50 is controlled by the controller 48 to reduce the fluid flow rate. In some cases, the physician may create a baseline level for visibility at which he or she prefers to initiate a field clearing flow of fluid and input these parameters into the fluid management system 10 via the touch screen interface 42 prior to the procedure. Once the baseline has been created, the fluid management system 10 may monitor the visual feed for variation in the picture and automatically adjust the fluid flow rate as necessary.

In order to adjust the fluid flow rate or the fluid pressure through the fluid management system 10, the fluid management unit may include one or more pressurization or flow-generating devices such as the inflow pump 50. In some embodiments, the inflow pump 50 may be a peristaltic pump. In some embodiments, the inflow pump 50 may include multiple pumps or more than one pump. The inflow pump 50 may be electrically driven and may receive power from a line source such as a wall outlet, an external or internal electrical storage device such as a disposable or rechargeable battery, and/or an internal power supply. The inflow pump 50 may operate at any desired speed sufficient to deliver fluid at a target pressure such as, for example, 5 mmHg to 50 mmHg, and/or at a target fluid flow rate. As noted herein, the inflow pump 50 may be automatically adjusted based on, for example, intracavity pressure and/or temperature readings within the treatment site and/or visual feedback from the medical device 20. The inflow pump 50 may also be manually adjusted via, for example, the optional foot pedal 46, the touch screen interface 42, or a separate fluid controller. While not explicitly shown, the fluid controller may be a separate user interface including buttons that allow the user to increase or decrease the speed and/or the output of the inflow pump 50. Alternatively, the fluid controller may be incorporated into the main processing device and receive input via the touch screen interface 42. In some embodiments, the fluid management system 10 may include multiple pumps having different flow capabilities. In some embodiments, a flow rate sensor 77 (e.g., FIG. 5) may be located before and/or after the inflow pump 50 to measure the actual fluid flow rate. The flow rate sensor 77 may be operably connected to the controller 48 and data from the flow rate sensor 77 may be used by the controller 48 to change selected system parameters.

The fluid flow rate and/or the fluid pressure of the fluid at any given time may be displayed on the display 44 to allow the operating room (OR) visibility for any changes. If the OR personnel notice a change in fluid flow rate and/or fluid pressure that is either too high or too low, the user may manually adjust the fluid flow rate and/or the fluid pressure back to a preferred level. This may happen, for example, as physicians insert and remove tools into the working channel of the medical device 20. The fluid management system 10 may also monitor and automatically adjust the fluid flow rate and/or the fluid pressure based on previously set parameters, as discussed herein. This feature may also be beneficial when fluid flow is provided manually such as an assistant injecting irrigation through a syringe.

In some embodiments, the fluid management system 10 may automatically adjust the fluid flow rate and/or the fluid pressure based on a measured intracavity temperature and/or a measured pressure, for example when the measured pressure reaches a preset pressure threshold. In some embodiments, the measured pressure may be an intracavity pressure measured within the treatment site, and the preset pressure threshold may be an intracavity pressure limit. The intracavity temperature and/or the intracavity pressure may be measured in situ using a temperature sensor 72 and/or a pressure sensor 74 mounted on the medical device 20 (e.g., FIG. 2) used in conjunction with the fluid management system 10. In some embodiments, the measured pressure may be a system pressure measured within the fluid management system 10, and the preset pressure threshold may be a system pressure limit. The system pressure may be measured within the fluid management system 10 using a pressure sensor 67 (e.g., FIG. 5) disposed within the fluid management system 10. In some embodiments, the fluid management system 10 may include pressure monitoring software so that the inflow pump 50 may be configured by the user to be automatically started, stopped, and/or speed adjusted by the fluid management system 10 to maintain a fluid pressure delivered to the treatment site at a target pressure and/or within a predetermined pressure range. For example, the pressure sensor 74 may detect intracavity pressure within the treatment site (for example, a kidney or uterus) and automatically alter the fluid flow rate and/or the fluid pressure within the fluid management system 10 based on the measured intracavity (e.g., intrarenal or intrauterine) pressure. If the intracavity pressure is too high, the fluid management system 10 may decrease the fluid flow rate and/or the fluid pressure and if the intracavity pressure is too low, the fluid management system 10 may increase the fluid flow rate and/or the fluid pressure.

Figure 3:
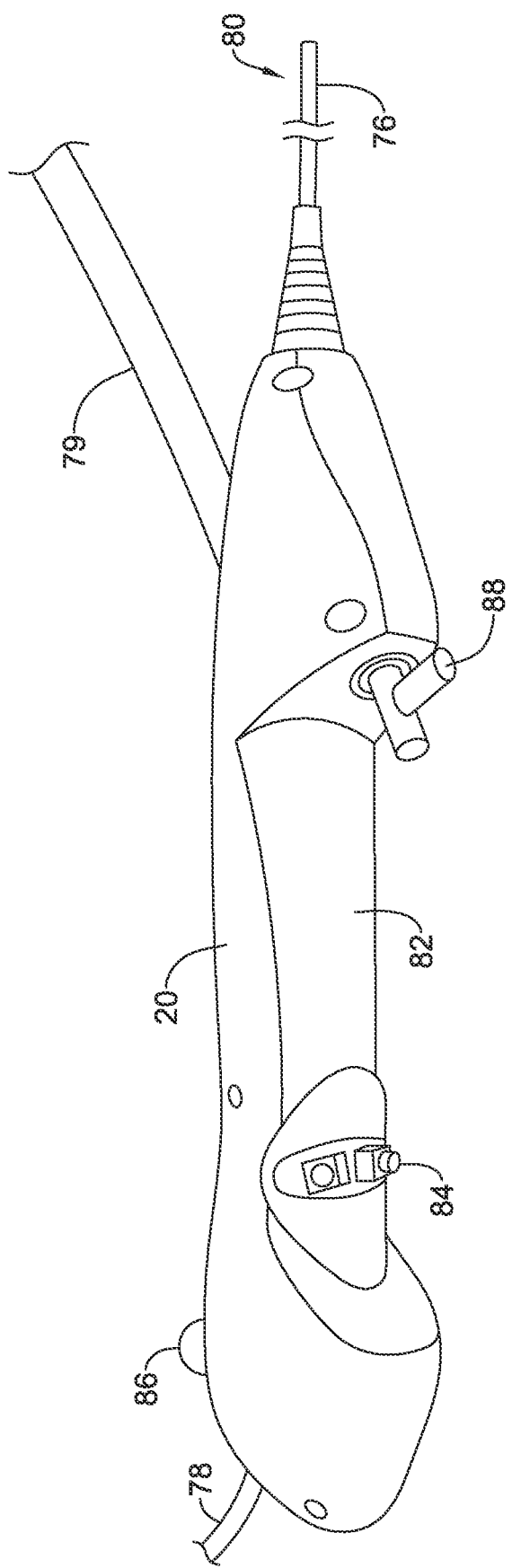
FIG. 3 illustrates selected aspects of the medical device of FIG. 2.
Figure 4:
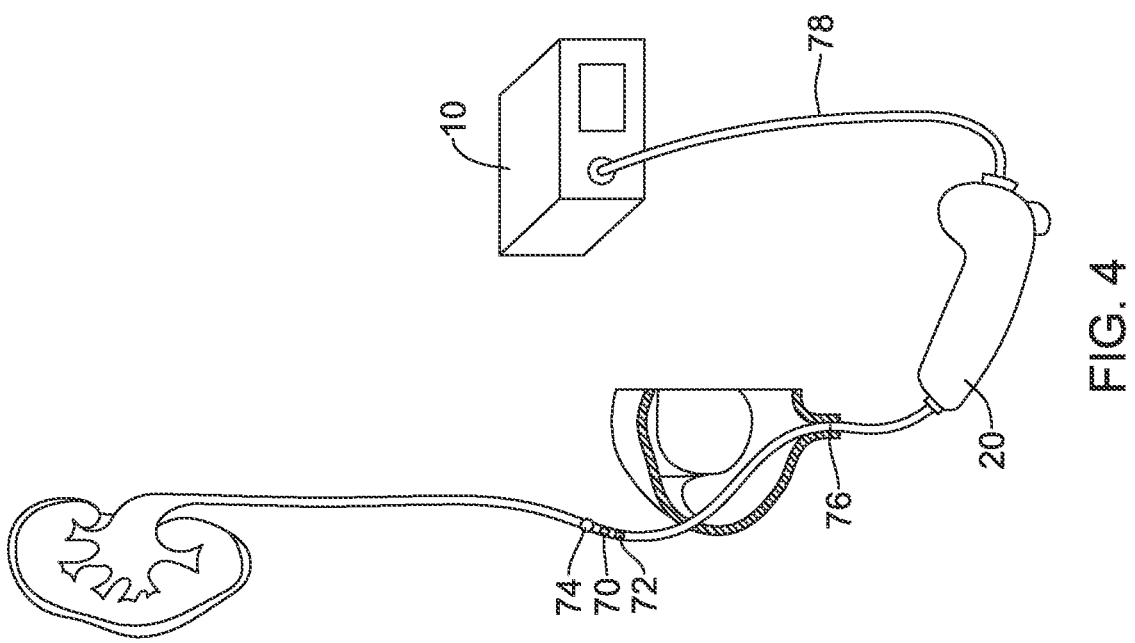
FIG. 4 is a schematic illustration of the medical device of FIG. 2 in situ.

FIGS. 2-4 illustrate aspects of the medical device 20 that may be used in conjunction with the fluid management system 10. In the illustrated embodiments, the medical device 20 may be a ureteroscope such as a LithoVue™ scope. However, other medical devices, such as another endoscope, may be used in addition to or in place of a ureteroscope. The medical device 20 may be configured to deliver fluid from the fluid management system 10 to the treatment site via an elongate shaft 76 configured to access the treatment site within the patient. In some embodiments, the inflow pump 50 may be in fluid communication with the elongate shaft 76. The elongate shaft 76 may include one or more working lumens for receiving a flow of fluid or other medical devices therethrough. The medical device 20 is connected to the fluid management system 10 via one or more supply line(s) 78 (e.g., a tube), as seen in FIGS. 1 and 4 for example.

In some embodiments, the medical device 20 may be in electronic communication with a workstation 81 via a wired connection 79. The workstation 81 may include a touch panel computer 83, an interface box 85 for receiving the wired connection 79, a cart 87, and a power supply 89, among other features. In some embodiments, the interface box 85 may be configured with a wired or wireless communication connection 91 with the controller 48 of the fluid management system 10. The touch panel computer 83 may include at least a display screen and an image processor. In some embodiments, the workstation 81 may be a multi-use component (e.g., used for more than one procedure) while the medical device 20 may be a single use device, although this is not required. In some embodiments, the workstation 81 may be omitted and the medical device 20 may be electronically coupled directly to the controller 48 of the fluid management system 10.

In some embodiments, the one or more supply line(s) 78 from the fluid management system 10 to the medical device 20 may be formed of a material the helps dampen the peristaltic motion created by the inflow pump 50. In some embodiments, the supply line(s) 78 may formed from small diameter tubing less than or equal to 1/16 inches (1.5875 millimeters) in diameter. However, it will be understood that tubing size may vary based on the application. The supply line(s) 78 and/or the tubing may be disposable and provided sterile and ready to use. Different types of tubing may be used for various functions within the fluid management system 10. For example, one type of tubing may be used for fluid heating and fluid flow control to the medical device 20 while another type of tubing may be used for irrigation within the body and/or the treatment site.

As seen in FIG. 2, the medical device 20 may include one or more sensors proximate a distal end 80 of the elongate shaft 76. For example, the medical device 20 may include a pressure sensor 74 at a distal tip of the elongate shaft 76 to measure intracavity pressure within the treatment site. The medical device 20 may also include other sensors such as, for example, a temperature sensor 72, a Fiber Bragg grating optical fiber 75 to detect stresses, and/or an antenna or electromagnetic sensor 93 (e.g., a position sensor). In an illustrative embodiment, the distal end 80 of the medical device 20 may also include at least one camera 70 to provide a visual feed to the user on the display screen of the touch panel computer 83. In another embodiment, the medical device 20 may include two cameras 70 having different communications requirements or protocols so that different information may be relayed to the user by each camera 70. When so provided, the user may switch back and forth between cameras 70 at will through the touch screen interface 42 and/or the touch panel computer 83. While not explicitly shown, the elongate shaft 76 may include one or more working lumens for receiving the fluid and/or other medical devices.

In some embodiments, the location of the distal end 80 of the elongate shaft 76 may be tracked during use. For example, a mapping and navigation system may include an operating table (or other procedural or examination table or chair, etc.) configured to act or function as an electromagnetic generator to generate a magnetic field of a known geometry. Alternatively, or additionally, an electromagnetic generator separate from the operating table may be provided. The operating table and/or the electromagnetic generator may be coupled to a control unit which may include among other features, a processor, a memory, a display, and an input means. A position sensor (e.g., the electromagnetic sensor 93, etc.) or other antenna, may be incorporated into the distal end 80 of the elongate shaft 76 of the medical device 20. The position sensor may be configured for use in sensing a location of the position sensor in the magnetic field of the mapping and navigation system. In some embodiments, the position sensor may be electronically coupled to the workstation 81. When the position sensor is in the magnetic field, the location of the position sensor can be mathematically determined relative to the electromagnetic field source (e.g., the operating table and/or the electromagnetic generator). The workstation 81 and the control unit may communicate to determine the position of the position sensor relative to the patient.

The medical device 20 includes a handle 82 coupled to a proximal end of the elongate shaft 76. The handle 82 may have a fluid flow on/off switch 84, which allows the user to control when fluid is flowing through the medical device 20 and into the treatment site. The handle 82 may further include other buttons 86 that perform other various functions. For example, in some embodiments, the handle 82 may include buttons to control the temperature of the fluid. It will be understood that while the exemplary embodiment describes a ureteroscope, the features detailed above may also be directly integrated into a cystoscope, an endoscope, a hysteroscope, or virtually any device with an image capability. In some embodiments, the medical device 20 may also include a drainage port 88 which may be connected to a drainage system. Some illustrative drainage systems are described in commonly assigned U.S. Patent Application Publication No. 2018/0361055, titled AUTOMATED FLUID MANAGEMENT SYSTEM, the disclosure of which is hereby incorporated by reference.

In some embodiments, the controller 48 may be configured to calculate a fluid deficit when the distal end 80 of the elongate shaft 76 is disposed within the patient, the fluid deficit being representative of fluid lost, absorbed by the patient, and/or otherwise unaccounted for during a procedure. In some embodiments, the controller 48 may be configured to notify a user when the total fluid deficit reaches a preset fluid deficit limit. In some embodiments, the controller 48 may be configured to stop the inflow pump 50 and/or the vacuum pump 24 when the total fluid deficit reaches the preset fluid deficit limit. In some embodiments, the controller 48 may be configured to notify a user when a total amount of fluid infused reaches a preset fluid infusion limit. In some embodiments, the controller 48 may be configured to stop the inflow pump 50 and/or the vacuum pump 24 when the total amount of fluid infused reaches the preset fluid infusion limit.

In some embodiments, the controller 48 may be configured to monitor the amount of fluid in the fluid supply source 34 through weight using, for example, the supply load cell 94, a scale, or other suitable means. The supply load cell 94 may be used by the controller 48 to determine a weight of the fluid supply source 34 attached to the fluid supply source hanger 32 to compare an initial amount of fluid in the fluid supply source 34 to a current amount of fluid remaining in the fluid supply source 34. The readout of the supply load cell 94 may be shown to the user on the display 44. As the procedure proceeds, the readout of the supply load cell 94 may be updated in real time to alert the physician to how much fluid is left in the fluid supply source 34 and this amount may then be used to determine how much fluid has been infused into the patient. In some embodiments, the amount of fluid remaining in the fluid supply source 34 may be shown. An alert may be shown on the display 44 with an audible signal when, for example, 10% of the fluid is left in the fluid supply source 34. In some embodiments, the supply load cell 94 may connect to the display 44 via a wireless (e.g., Wi-Fi) signal. In some embodiments, the supply load cell 94 may be connected to the display 44 via a hard wire connection. During the procedure, if the fluid supply source 34 becomes empty, it may be replaced with a full or unused fluid supply source 34.

Similarly, the controller 48 may be configured to monitor the amount of fluid in the collection container 26 through weight using, for example, the collection load cell 25, a scale, or other suitable means. The collection load cell 25 may be used by the controller 48 to determine a weight of the collection container 26 to compare an initial amount of fluid in the collection container 26 to a current amount of fluid in the collection container 26. The readout of the collection load cell 25 may be shown to the user on the display 44. As the procedure proceeds, the readout of the collection load cell 25 may be updated in real time to alert the physician to how much fluid is in the collection container 26 and this amount may then be used to determine how much fluid has been collected from the patient and/or the collection drape 28. In some embodiments, the amount of fluid in the collection container 26 may be shown. An alert may be shown on the display 44 with an audible signal when, for example, 10% of an initial empty volume is left in the collection container 26. In some embodiments, the collection load cell 25 may connect to the display 44 via a wireless (e.g., Wi-Fi) signal. In some embodiments, the collection load cell 25 may be connected to the display 44 via a hard wire connection. During the procedure, if the collection container 26 becomes full, it may be emptied and placed back into use, or the collection container 26 may be replaced by an empty collection container.

Figure 5:
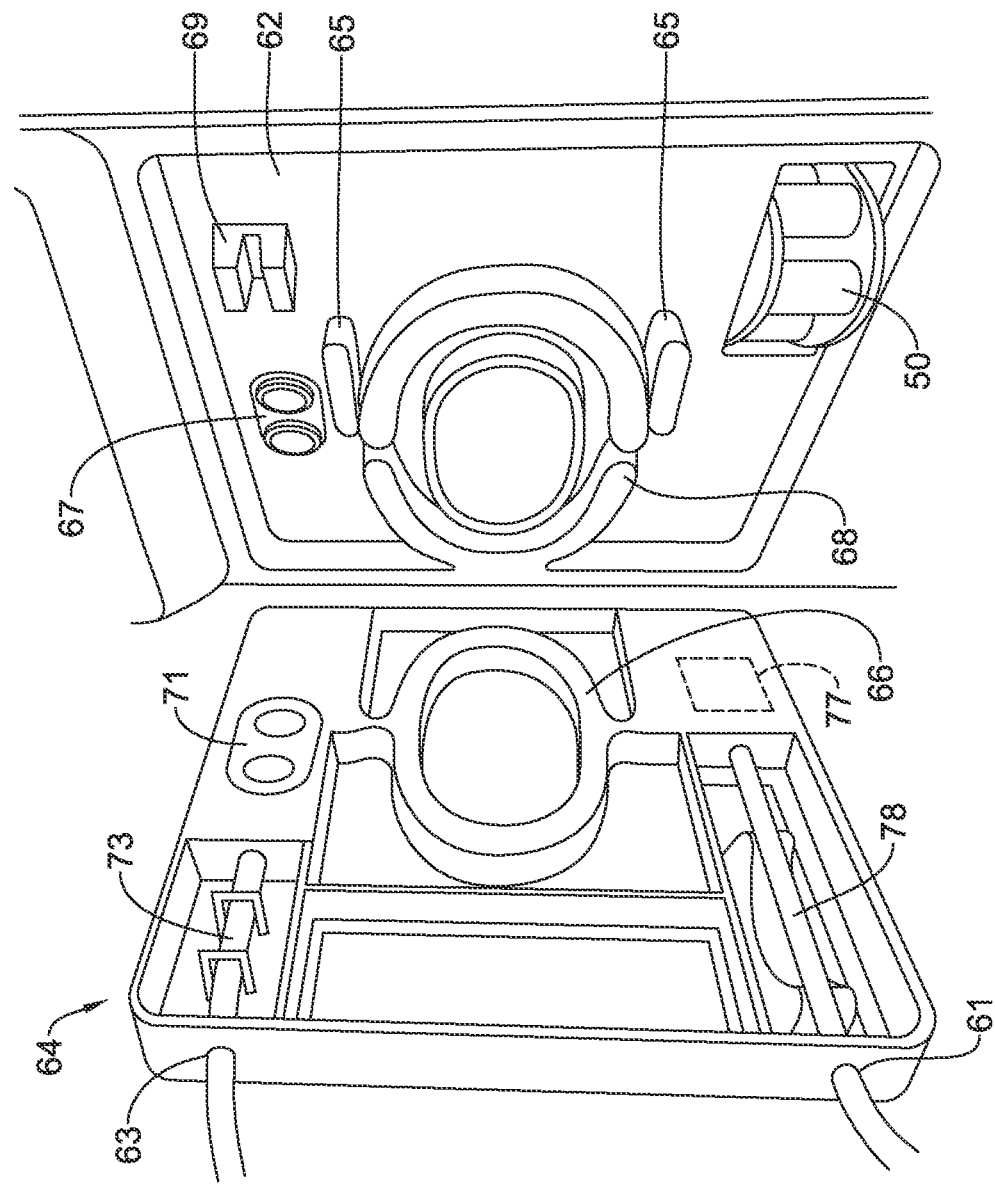
FIG. 5 is a partial perspective view illustrating selected aspects of a heater assembly and cassette of the system of FIG. 1.

In some embodiments, the fluid management system 10 may include a fluid warming system 60, as shown in FIG. 5, for heating fluid to be delivered to the patient. The fluid warming system 60 may include a heater 62 and a heater cassette 64. The heater cassette 64 may be configured to be a single use heater cassette 64 while the heater 62 may be reused for multiple procedures. For example, the heater cassette 64 may isolate fluid flow such that the heater 62 may be reused with minimal maintenance. The heater cassette 64 may be formed of, for example, polycarbonate or any high heat rated biocompatible plastic and is formed as a single unitary and/or monolithic piece or a plurality of pieces permanently bonded to one another. In some embodiments, the heater cassette 64 may include a fluid inlet port 61 and a fluid outlet port 63 located at a lateral side of the heater cassette 64. The fluid inlet port 61 and the fluid outlet port 63 may each be configured to couple to the supply line(s) 78 of the fluid management system 10. For example, the fluid inlet port 61 may couple the fluid supply source 34 and the fluid warming system 60 (via the inflow pump 50) while the fluid outlet port 63 may couple the fluid warming system 60 with the medical device 20, each via the supply line(s) 78.

In some embodiments, the heater cassette 64 may include an internal flow path along a channel through which fluid may flow from the fluid inlet port 61 to the fluid outlet port 63. The heater cassette 64 may include one fluid path or multiple fluid paths. In some embodiments, the channel may pass through a susceptor 66 which may allow the fluid to be heated via induction heating. When the heater cassette 64 is coupled with the heater 62, the susceptor 66 may be configured to be positioned within an induction coil 68. Other fluid warming system configurations and methods may also be used, as desired. For example, the heater 62 may include one or more heat sources such as, for example a platen system or an inline coil in the supply line(s) 78 using electrical energy. Heating may be specifically designed and tailored to the flow rates required in the specific application of the fluid management system 10. Some illustrative fluid warming systems are described in described in commonly assigned U.S. Patent Application Publication No. 2018/0361055, titled AUTOMATED FLUID MANAGEMENT SYSTEM, the entire disclosure of which is hereby incorporated by reference.

While not explicitly shown, the fluid warming system 60 may include a heater user interface separate from the touch screen interface 42. The heater user interface may simply be a display screen providing a digital display of the internal temperature of the heater 62. In another embodiment, the user interface may also include temperature adjustment buttons to increase or decrease the temperature of the heater 62. In this embodiment, the heater user interface and/or the display screen may indicate the current temperature of the heater 62 as well as the target temperature to be reached. It is noted that all information output from the fluid warming system 60 may be transmitted directly to the display 44 such that no heater user interface is necessary.

The fluid warming system 60 may include one or more sensors configured to monitor the fluid flowing therethrough. For example, temperature sensors 65 may be mounted in the fluid warming system 60 such that they detect the temperature of the fluid flowing through the heater cassette 64. The temperature sensors 65 may be located at or near the fluid inlet port 61 and/or the fluid outlet port 63. In some embodiments, the temperature sensors 65 may be mounted so that they detect the temperature of fluid flowing through the heater cassette 64 prior to the fluid entering the susceptor 66 and after fluid exits the susceptor 66. In some embodiments, additional sensors may be located at a medial portion of the susceptor 66 so that they detect a progression of temperature increase of the fluid in the heater cassette 64. The temperature sensors 65 may remotely send any information to the display 44 or they may send information to heater user interface and/or the display screen thereof, if so provided. In another embodiment, the temperature sensors 65 may be hardwired with the heater user interface (if provided) which is then able to remotely transmit desired information to the display 44. Alternatively, or additionally, the temperature sensors 65 may be hardwired to and/or with the controller 48.

The heater 62 may further include a pressure sensor 67 configured to monitor system pressure and/or a bubble sensor 69 configured to monitor the fluid flowing through the system for bubbles. The heater cassette 64 may include a corresponding pressure sensor interface 71 and bubble sensor interface 73 that allow the pressure sensor 67 and the bubble sensor 69, respectively, to monitor the fluid flowing through the heater cassette 64 when the heater cassette 64 is coupled with the fluid warming system 60. The pressure sensor 67 and/or the bubble sensor 69 may remotely send any information to the controller 48, the display 44, and/or they may send information to the heater user interface and/or the display screen thereof, if so provided. In another embodiment, the pressure sensor 67 and/or the bubble sensor 69 may be hardwired with the heater user interface (if provided) which is then able to remotely transmit desired information to the display 44. Alternatively, or additionally, the pressure sensor 67 and/or the bubble sensor 69 may be hardwired to and/or with the controller 48.

Figure 6A:
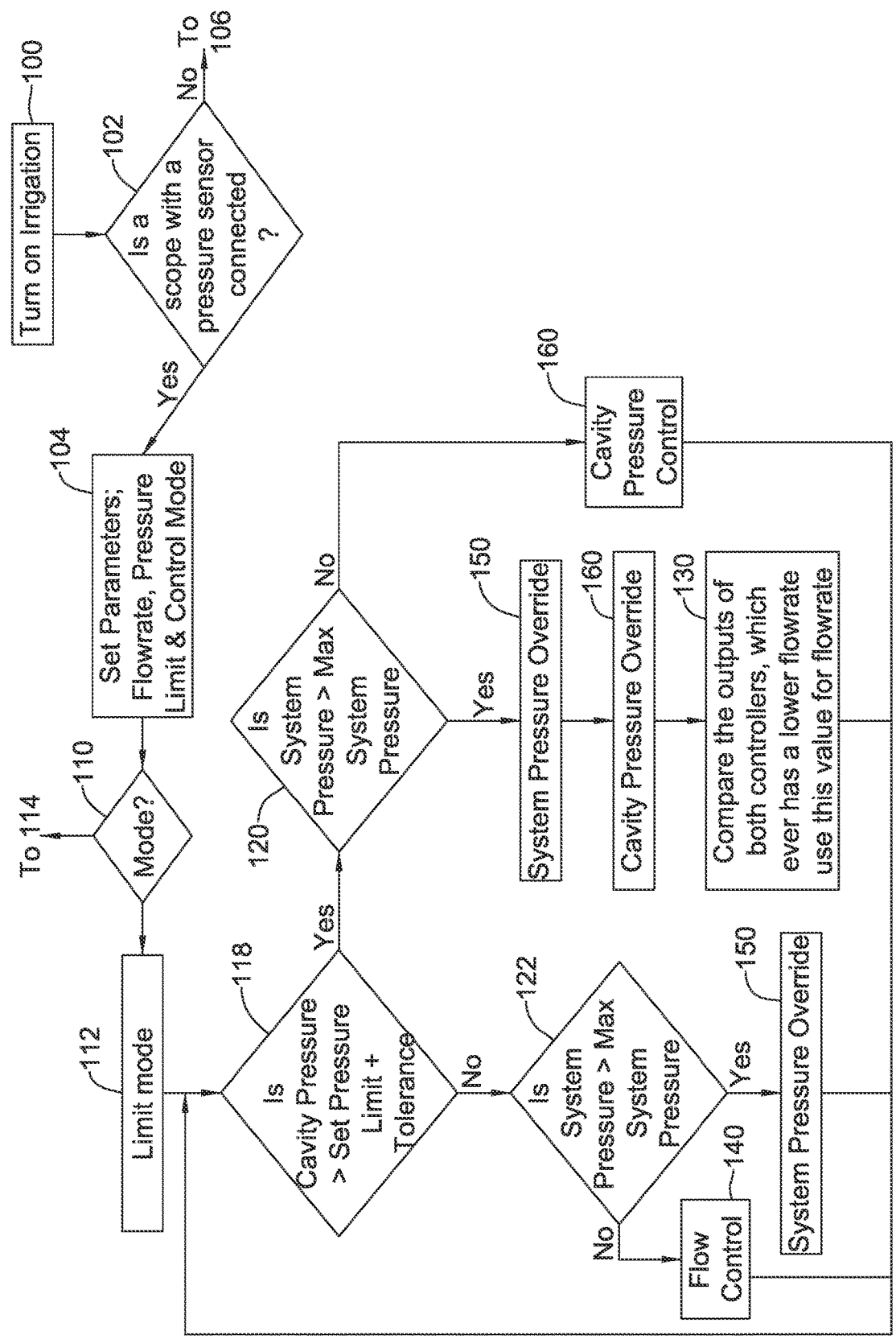
FIGS. 6A-6C is a flow chart illustrating interactions between different operating modes of the fluid management system.
Figure 6B:
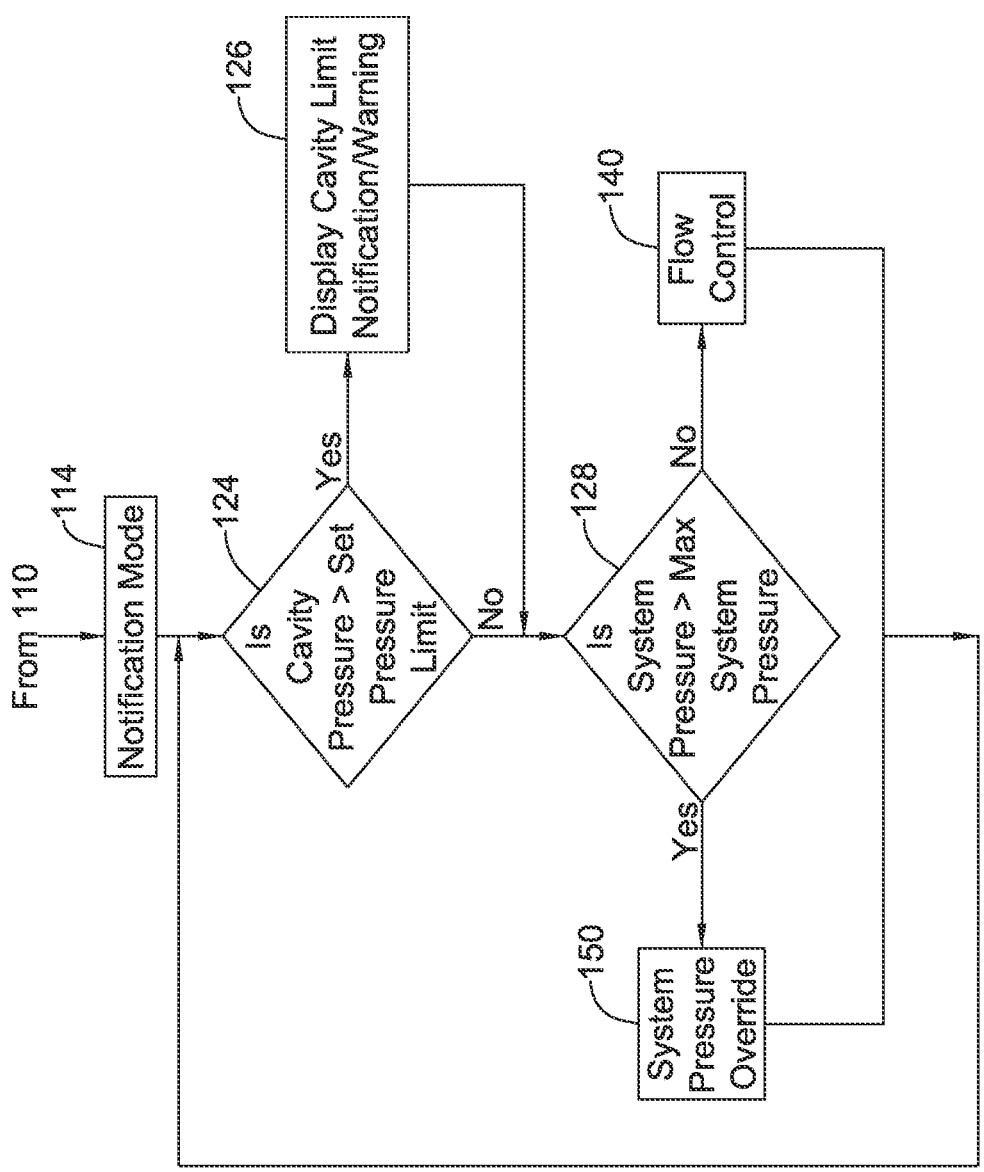
Figure 6C:
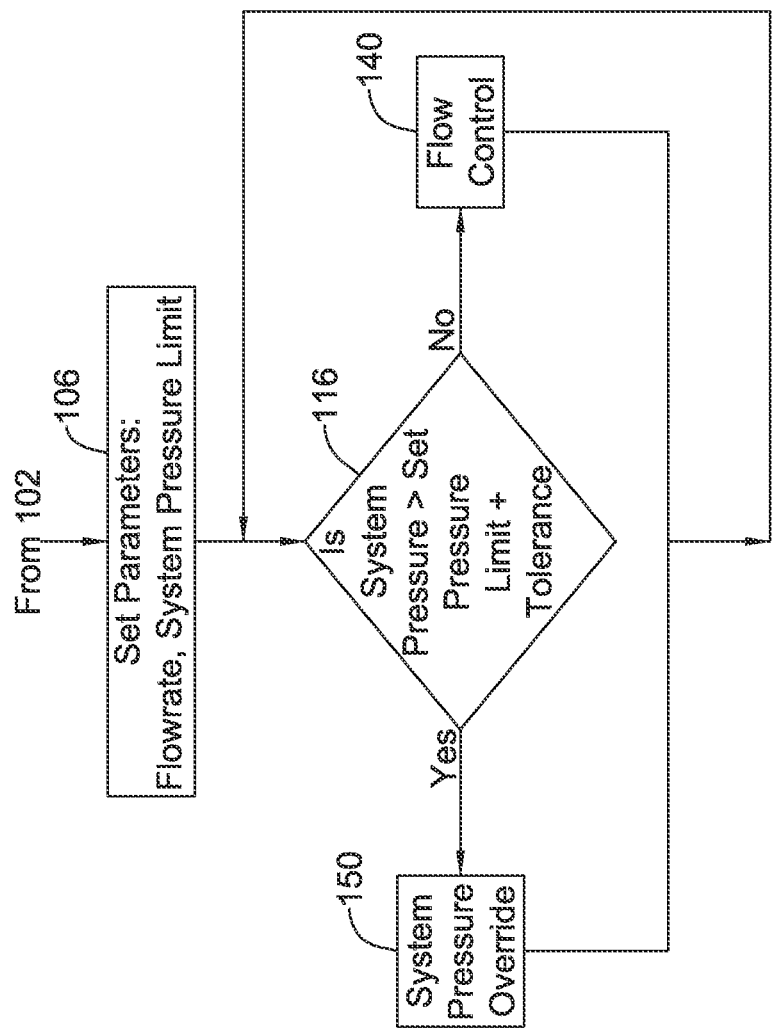

FIGS. 6A-6C illustrate a flow chart showing interactions, decisions, and/or methods associated with the fluid management system 10. In the current example, the controller 48 is configured to operate the at a target flow rate in a flow control mode. In some situations, the physician may find it beneficial to maintain the target flow rate whenever possible—to maintain a clear field of view, for example. In the flow control mode, the controller 48 may attempt to maintain the target flow rate regardless of other factors or settings, until or unless certain predetermined conditions are met. For example, in the flow control mode, the controller 48 may be configured to "sacrifice" other measures and/or characteristics to maintain the target flow rate.

Initially, the fluid management system 10 may be initialized and/or turned on. This is shown on FIG. 6A at reference 100. Next, the controller 48 may check to determine what type of endoscope and/or medical device 20 is connected to the fluid management system 10. It is possible to use the fluid management system 10 with a medical device 20 that is configured to monitor intracavity pressure using a pressure sensor 74. If the medical device 20 is so configured, the controller 48 may be operated in a mode in which intracavity pressure and system pressure may be monitored and/or used to affect control of the fluid management system 10, as shown in FIG. 6A. Accordingly, the controller 48 then permits the user to set selected operating and/or system parameters at reference 104, such as target flow rate, pressure limit (e.g., intracavity pressure limit and/or system pressure limit), and/or what control mode to operate in. In some embodiments, one or more of the operating and/or system parameters may be preset, pre-loaded, and/or hard-coded into the controller 48, and thus not available for manual selection or input. Other operating and/or system parameters are also contemplated for user selection.

At reference 110, the controller 48 may be configured to query the operating and/or system parameters input at reference 104 to determine whether to operate in a Limit mode 112 or a Notification mode 114. In the Limit mode 112, the controller 48 may be configured to maintain the target flow rate in the flow control mode by default and will attempt to maintain the target flow rate whenever possible while monitoring a measured pressure (e.g., intracavity pressure and/or system pressure) communicated to the controller 48 from the pressure sensor 74 and/or the pressure sensor 67. When the measured pressure reaches a preset pressure threshold, the controller 48 may be configured to automatically switch from the flow control mode to a pressure override mode in which the controller 48 automatically reduces the flow rate below the target flow rate to return the measured pressure at or below the preset pressure threshold. In some embodiments, the controller 48 may be configured to display a notification on the display 44 informing the user that the controller 48 has switched from the flow control mode to the pressure override mode when the measured pressure reaches and/or rises above the preset pressure threshold. In some embodiments, the measured pressure is the intracavity pressure measured within the treatment site. In at least some embodiments, the intracavity pressure may be measured using the pressure sensor 74. In some embodiments where the measured pressure is the intracavity pressure, the preset pressure threshold may be the intracavity pressure limit set at reference 104. In some embodiments, the measured pressure is the system pressure measured within the fluid management system 10. In at least some embodiments, the system pressure may be measured using the pressure sensor 67. In some embodiments where the measured pressure is the system pressure, the preset pressure threshold may be the system pressure limit set at reference 104.

In some embodiments, the controller 48 may be configured to display a prompt on the display 44 informing the user that the controller 48 has switched from the flow control mode to the pressure override mode when the measured pressure reaches and/or rises above the preset pressure threshold and giving the user an option to override and/or ignore the preset pressure threshold, thereby returning the controller 48 to the flow control mode and permitting the measured pressure to continue to rise above and/or remain above the preset pressure threshold. The controller 48 may be configured to automatically switch from the flow control mode to the pressure override mode unless the user has expressly acknowledged the option to override and/or ignore the preset pressure threshold and/or expressly directed the controller 48 to return to the flow control mode.

At reference 118 within the Limit mode 112, the controller 48 may compare the measured pressure (e.g., the intracavity pressure) plus a preset tolerance (e.g., 5%, 10%, 15%, 25%, etc.) to the intracavity pressure limit set at reference 104. If the intracavity pressure plus the preset tolerance is less than the intracavity pressure limit set at reference 104, the controller 48 may proceed to reference 122 and then compare the system pressure to the system pressure limit set at reference 104. If the system pressure is less than the system pressure limit, the controller 48 may continue to operate in the flow control mode 140 or the controller 48 may be configured to automatically switch from the pressure override mode (as discussed herein) back to the flow control mode 140 when the measured pressure (e.g., the intracavity pressure and/or the system pressure) falls below the preset pressure threshold. In the pressure override mode, the controller 48 may be configured to calculate a reduced flow rate that depends on the target flow rate, the actual flow rate, and/or the measured pressure relative to the preset pressure threshold, and then operate at the reduced flow rate to return the measured pressure at or below the preset pressure threshold while continuing to monitor the measured pressure.

If the measured pressure (e.g., the intracavity pressure) plus the preset tolerance is greater than (e.g., exceeds) the intracavity pressure limit set at reference 104, the controller 48 may proceed to reference 120 and then compare the system pressure to the system pressure limit set at reference 104. If the system pressure is less than the system pressure limit, the controller 48 may be configured to automatically switch to a cavity pressure override mode 160, wherein the controller automatically reduces the flow rate below the target flow rate to return the intracavity pressure at or below the intracavity pressure limit. In some embodiments, the controller 48 may be configured to display a notification on the display 44 informing the user that the controller 48 has switched from the flow control mode to the cavity pressure override mode when the intracavity pressure reaches and/or rises above the intracavity pressure limit. In some embodiments, the controller 48 may be configured to display a prompt on the display 44 informing the user that the controller 48 has switched from the flow control mode to the cavity pressure override mode when the intracavity pressure reaches and/or rises above the intracavity pressure limit and giving the user an option to override and/or ignore the intracavity pressure limit, thereby returning the controller 48 to the flow control mode and permitting the intracavity pressure to continue to rise above and/or remain above the intracavity pressure limit. The controller 48 may be configured to automatically switch from the flow control mode to the cavity pressure override mode unless the user has expressly acknowledged the option to override and/or ignore the intracavity pressure limit and/or expressly directed the controller 48 to return to the flow control mode. The controller 48 may then proceed back to reference 118 and begin the queries again.

If the system pressure is greater than (e.g., exceeds) the system pressure limit set at reference 104, the controller 48 may be configured to automatically switch to a system pressure override mode 150, wherein the controller automatically reduces the flow rate below the target flow rate to return the system pressure at or below the system pressure limit. In some embodiments, the controller 48 may be configured to display a notification on the display 44 informing the user that the controller 48 has switched from the flow control mode to the system pressure override mode when the system pressure reaches and/or rises above the system pressure limit. In some embodiments, the controller 48 may be configured to display a prompt on the display 44 informing the user that the controller 48 has switched from the flow control mode to the system pressure override mode when the system pressure reaches and/or rises above the system pressure limit and giving the user an option to override and/or ignore the system pressure limit, thereby returning the controller 48 to the flow control mode and permitting the system pressure to continue to rise above and/or remain above the system pressure limit. The controller 48 may be configured to automatically switch from the flow control mode to the system pressure override mode unless the user has expressly acknowledged the option to override and/or ignore the system pressure limit and/or expressly directed the controller 48 to return to the flow control mode. The controller 48 may be configured to compare the reduced flow rate of the system pressure override mode 150 to the reduced flow rate of the cavity pressure override mode 160 and then operate at the lower of the reduced flow rates. The controller 48 may then proceed back to reference 118 and begin the queries again.

Returning to reference 110, the controller 48 may be configured to query the operating and/or system parameters input at reference 104 to determine whether to operate in the Limit mode 112 or the Notification mode 114. In the Notification mode 114, shown in FIG. 6B, the controller 48 may be configured to maintain the target flow rate in the flow control mode by default and will attempt to maintain the target flow rate whenever possible while monitoring a measured pressure (e.g., intracavity pressure and/or system pressure) communicated to the controller 48 from the pressure sensor 74 and/or the pressure sensor 67.

At reference 124 within the Notification mode 114, the controller 48 may compare the measured pressure (e.g., the intracavity pressure) plus a preset tolerance (e.g., 5%, 10%, 15%, 25%, etc.) to the intracavity pressure limit set at reference 104. However, in contrast to the Limit mode 112, when the measured pressure (e.g., the intracavity pressure) plus the preset tolerance is greater than (e.g., exceeds) the intracavity pressure limit set at reference 104, the controller 48 may be configured to display a Cavity Limit Notification/Warning 126 on the display 44. In some embodiments, the Cavity Limit Notification/Warning 126 may be accompanied by an audible alert. This will notify the user of the condition without making any changes to the flow rate. For example, the controller 48 will still continue to maintain the target flow rate.

Next, or if the intracavity pressure plus the preset tolerance is less than the intracavity pressure limit set at reference 104, the controller 48 may proceed to reference 128 and then compare the system pressure to the system pressure limit set at reference 104. If the system pressure is less than the system pressure limit, the controller 48 may continue to operate in the flow control mode 140. If the system pressure is greater than (e.g., exceeds) the system pressure limit set at reference 104, the controller 48 may be configured to automatically switch to a system pressure override mode 150, wherein the controller automatically reduces the flow rate below the target flow rate to return the system pressure at or below the system pressure limit. In some embodiments, the controller 48 may be configured to display a notification on the display 44 informing the user that the controller 48 has switched from the flow control mode 140 to the system pressure override mode 150 when the system pressure reaches and/or rises above the system pressure limit. In some embodiments, the controller 48 may be configured to display a prompt on the display 44 informing the user that the controller 48 has switched from the flow control mode 140 to the system pressure override mode 150 when the system pressure reaches and/or rises above the system pressure limit and giving the user an option to override and/or ignore the system pressure limit, thereby returning the controller 48 to the flow control mode 140 and permitting the system pressure to continue to rise above and/or remain above the system pressure limit. The controller 48 may be configured to automatically switch from the flow control mode 140 to the system pressure override mode 150 unless the user has expressly acknowledged the option to override and/or ignore the system pressure limit and/or expressly directed the controller 48 to return to the flow control mode 140. The controller 48 may then proceed back to reference 124 and begin the queries again.

It is also possible to use the fluid management system 10 with a medical device 20 that does not have a pressure sensor configured to detect intracavity pressure associated therewith. If the medical device 20 is so configured, the controller 48 may be limited to a mode in which only system pressure may be monitored and/or used to affect control of the fluid management system 10, as illustrated in FIG. 6C. At reference 106, the controller 48 may permit the user to set selected operating and/or system parameters at reference 104, such as target flow rate and the system pressure limit. In some embodiments, one or more of the operating and/or system parameters may be preset, pre-loaded, and/or hard-coded into the controller 48, and thus not available for manual selection or input. Other operating and/or system parameters are also contemplated for user selection.

The controller 48 may be configured to maintain the target flow rate in the flow control mode by default and will attempt to maintain the target flow rate whenever possible while monitoring a measured pressure (e.g., system pressure) communicated to the controller 48 from the pressure sensor 67. At reference 116, the controller 48 may compare the measured pressure (e.g., the system pressure) plus a preset tolerance (e.g., 5%, 10%, 15%, 25%, etc.) to the system pressure limit set at reference 106. If the measured pressure is less than the system pressure limit, the controller 48 may continue to operate in the flow control mode 140. If the measured pressure is greater than (e.g., exceeds) the system pressure limit set at reference 106, the controller 48 may be configured to automatically switch to a system pressure override mode 150, wherein the controller automatically reduces the flow rate below the target flow rate to return the system pressure at or below the system pressure limit. In some embodiments, the controller 48 may be configured to display a notification on the display 44 informing the user that the controller 48 has switched from the flow control mode 140 to the system pressure override mode 150 when the system pressure reaches and/or rises above the system pressure limit. In some embodiments, the controller 48 may be configured to display a prompt on the display 44 informing the user that the controller 48 has switched from the flow control mode 140 to the system pressure override mode 150 when the system pressure reaches and/or rises above the system pressure limit and giving the user an option to override and/or ignore the system pressure limit, thereby returning the controller 48 to the flow control mode 140 and permitting the system pressure to continue to rise above and/or remain above the system pressure limit. The controller 48 may be configured to automatically switch from the flow control mode 140 to the system pressure override mode 150 unless the user has expressly acknowledged the option to override and/or ignore the system pressure limit and/or expressly directed the controller 48 to return to the flow control mode 140. The controller 48 may then proceed back to reference 116 and begin the queries again.

Figure 7:
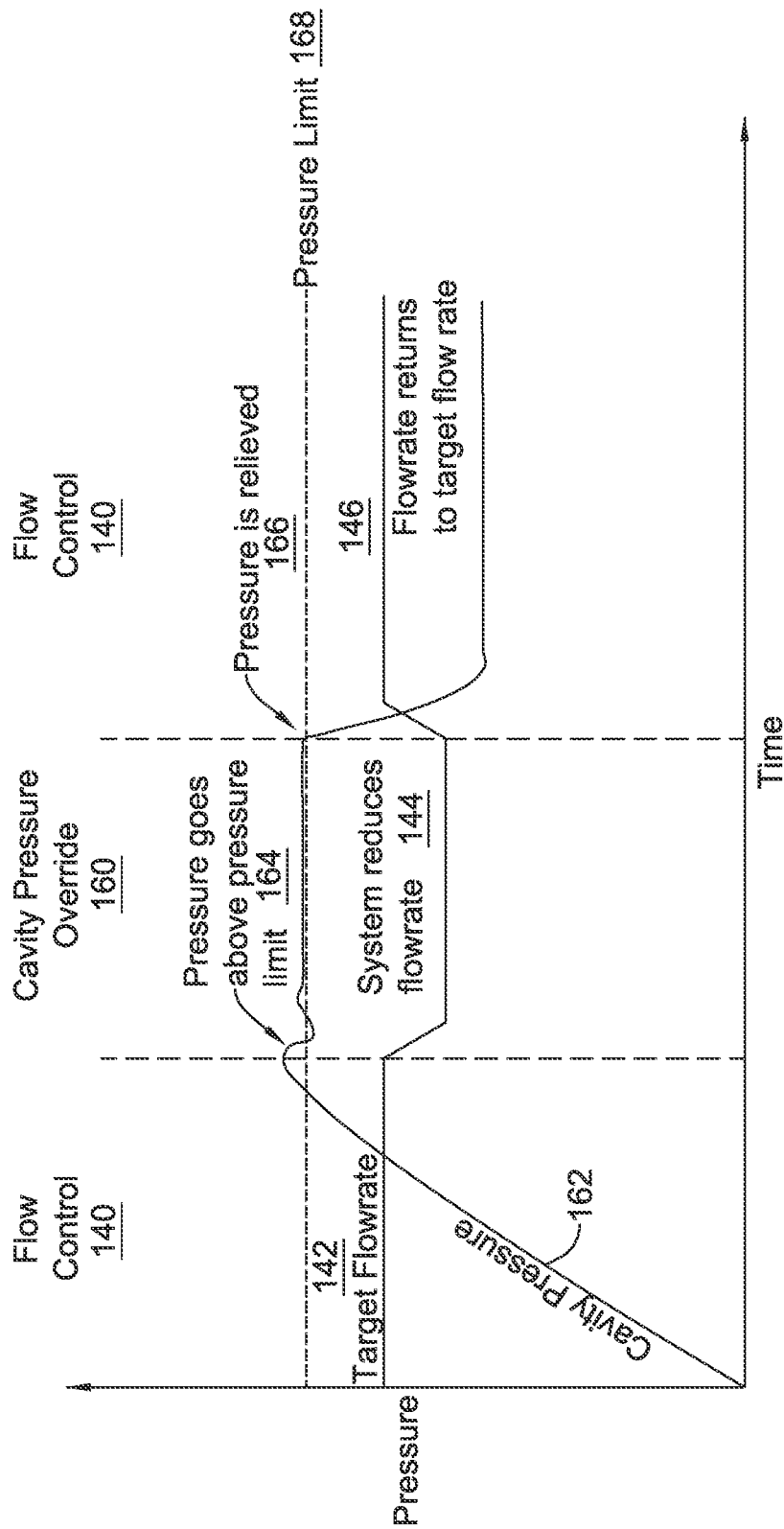
FIGS. 7-10 are graphs illustrating interactions between different operating modes of the fluid management system.
Figure 8:
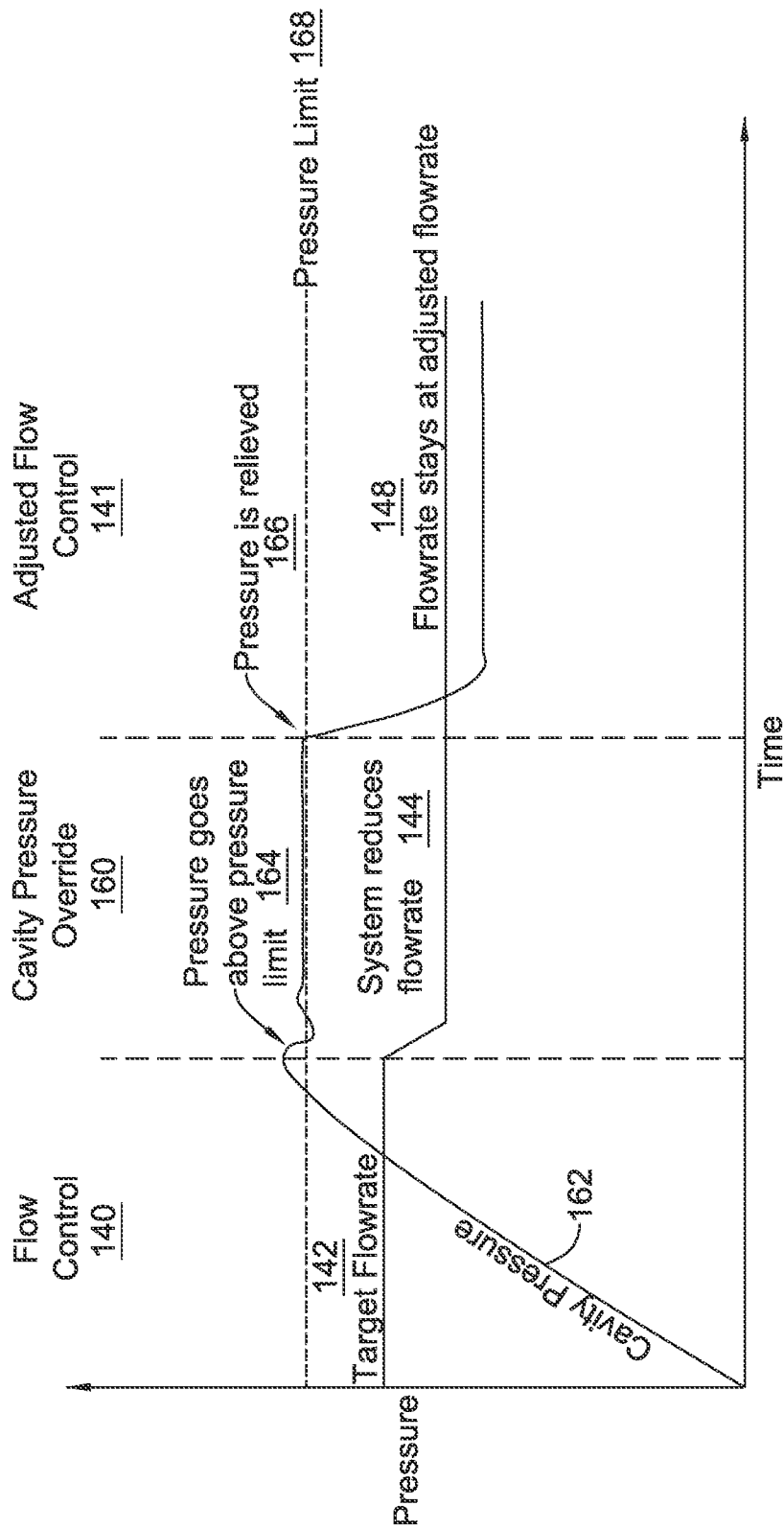

FIGS. 7 and 8 illustrate aspects of the controller 48 switching into and out of the cavity pressure override mode 160. The graphs show pressure on the vertical axis and time on the horizontal axis. Initially, when the fluid management system 10 is turned on, the measured pressure (e.g., intracavity pressure 162) may be zero or very close to zero. The target flow rate 142 and/or the intracavity pressure limit 168 may be input into the controller 48 by the user at reference 104 (e.g., FIG. 6A), which generally coincides with the vertical axis and/or the zero point along the horizontal axis. As the fluid management system 10 and/or the controller operates at the target flow rate 142, the intracavity pressure 162 may increase. The increase may be linear, exponential, parabolic, and/or irregular, with rises and dips over time, depending on the procedure being performed, actions undertaken during the procedure, changes in conditions, etc.

At some point in time, the measured intracavity pressure 162 may rise above the intracavity pressure limit 168, shown on the graphs at reference 164. After the measured intracavity pressure 162 has risen above the intracavity pressure limit 168, and/or has risen above the intracavity pressure limit 168 plus the preset tolerance (e.g., 5%, 10%, 15%, 25%, etc.) to the intracavity pressure limit set at reference 104, the controller 48 may be configured to switch to the cavity pressure override mode 160 in which the controller 48 automatically reduces the flow rate below the target flow rate 142, as shown at reference 144 (e.g., the reduced flow rate), to return the measured pressure (e.g., the intracavity pressure 162) at or below the preset pressure threshold (e.g., the intracavity pressure limit 168). In some embodiments, the controller 48 may be configured to display a notification on the display 44 informing the user that the controller 48 has switched from the flow control mode 140 to the cavity pressure override mode 160 when the measured intracavity pressure 162 reaches and/or rises above the intracavity pressure limit 168. In some embodiments, the controller 48 may be configured to display a prompt on the display 44 informing the user that the controller 48 has switched from the flow control mode 140 to the cavity pressure override mode 160 when the measured intracavity pressure 162 reaches and/or rises above the intracavity pressure limit 168 and giving the user an option to override and/or ignore the intracavity pressure limit 168, thereby returning the controller 48 to the flow control mode 140 and permitting the measured intracavity pressure 162 to continue to rise above and/or remain above the intracavity pressure limit 168. The controller 48 may be configured to automatically switch from the flow control mode 140 to the cavity pressure override mode 160 unless the user has expressly acknowledged the option to override and/or ignore the intracavity pressure limit 168 and/or expressly directed the controller 48 to return to the flow control mode 140.

In some embodiments, when the measured pressure (e.g., intracavity pressure 162) is relieved and/or falls below the preset pressure threshold (e.g., the intracavity pressure limit 168), as shown at reference 166, the controller 48 may be configured to switch from the cavity pressure override mode 160 back to the flow control mode 140. In some embodiments, the controller 48 may be configured to display a prompt of the display 44 asking if the user wants to switch out of the cavity pressure override mode 160 when the measured pressure is relieved and/or falls below the preset pressure threshold. In some embodiments, the prompt may ask if the user wants to switch from the cavity pressure override mode 160 back to the flow control mode 140 or to an adjusted flow control mode 141. In at least some embodiments, when switching back to the flow control mode 140, the flow rate may return to the target flow rate 142 configured by and/or associated with the flow control mode 140, as shown at reference 146 in FIG. 7. In some embodiments, the controller 48 may be configured to display a prompt on the display 44 asking if the user wants to switch back to the flow control mode 140 when the measured pressure (e.g., intracavity pressure 162) falls below the preset pressure threshold. In some embodiments, the controller 48 may be configured to display a notification on the display 44 and automatically switch from the cavity pressure override mode 160 back to the flow control mode 140 when the measured pressure (e.g., intracavity pressure 162) falls below the preset pressure threshold.

In some embodiments, when the measured pressure (e.g., intracavity pressure 162) is relieved and/or falls below the preset pressure threshold (e.g., the intracavity pressure limit 168), as shown at reference 166, the controller 48 may be configured to switch from the cavity pressure override mode 160 to the adjusted flow control mode 141. The controller 48 may be configured to operate at the reduced flow rate of the cavity pressure override mode 160 when in the adjusted flow control mode 141, as shown at reference 148 in FIG. 8. For example, in the adjusted flow control mode 141, the flow rate may be thereafter maintained at the reduced flow rate associated with the cavity pressure override mode 160. In some embodiments, the controller 48 may be configured to display a prompt on the display 44 asking if the user wants to switch to the adjusted flow control mode 141 when the measured pressure (e.g., intracavity pressure 162) falls below the preset pressure threshold. In some embodiments, the controller 48 may be configured to display a notification on the display 44 and automatically switch from the cavity pressure override mode 160 to the adjusted flow control mode 141 when the measured pressure (e.g., intracavity pressure 162) falls below the preset pressure threshold.

Figure 9:
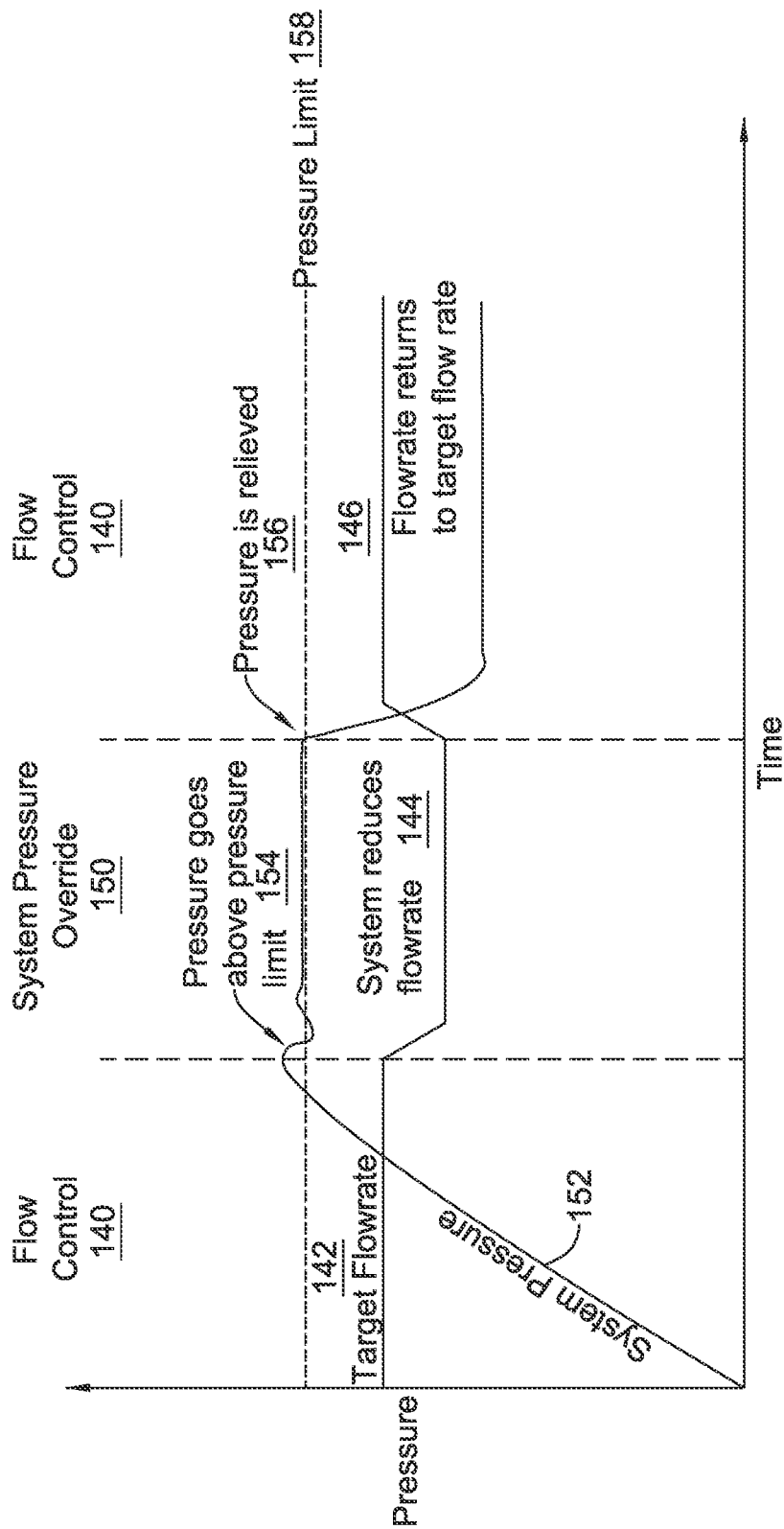
Figure 10:
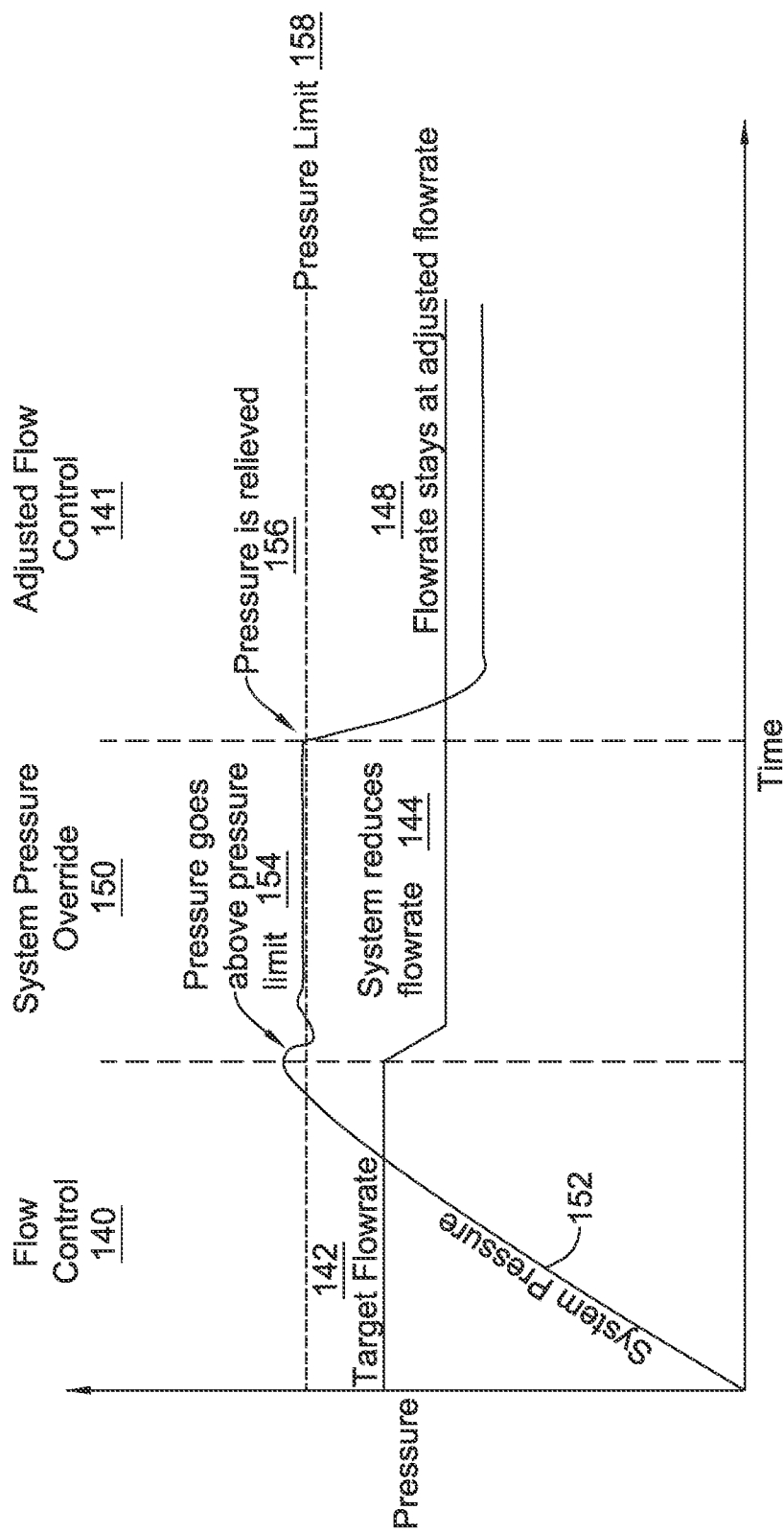

FIGS. 9 and 10 illustrate aspects of the controller 48 switching into and out of the system pressure override mode 150. The graphs show pressure on the vertical axis and time on the horizontal axis. Initially, when the fluid management system 10 is turned on, the measured pressure (e.g., system pressure 152) may be zero or very close to zero. The target flow rate 142 and/or the system pressure limit 158 may be input into the controller 48 by the user at reference 104 (e.g., FIG. 6A) or reference 106 (e.g., FIG. 6C), which generally coincides with the vertical axis and/or the zero point along the horizontal axis. As the fluid management system 10 and/or the controller operates at the target flow rate 142, the system pressure 152 may increase. The increase may be linear, exponential, parabolic, and/or irregular, with rises and dips over time, depending on the procedure being performed, actions undertaken during the procedure, changes in conditions, etc.

At some point in time, the measured system pressure 152 may rise above the system pressure limit 158, shown on the graphs at reference 154. After the measured system pressure 152 has risen above the system pressure limit 158, and/or has risen above the system pressure limit 158 plus the preset tolerance (e.g., 5%, 10%, 15%, 25%, etc.) to the system pressure limit set at reference 104/106, the controller 48 may be configured to switch to the system pressure override mode 150 in which the controller 48 automatically reduces the flow rate below the target flow rate 142, as shown at reference 144 (e.g., the reduced flow rate), to return the measured pressure (e.g., the system pressure 152) at or below the preset pressure threshold (e.g., the system pressure limit 158). In some embodiments, the controller 48 may be configured to display a notification on the display 44 informing the user that the controller 48 has switched from the flow control mode 140 to the system pressure override mode 150 when the measured system pressure 152 reaches and/or rises above the system pressure limit 158. In some embodiments, the controller 48 may be configured to display a prompt on the display 44 informing the user that the controller 48 has switched from the flow control mode 140 to the system pressure override mode 150 when the measured system pressure 152 reaches and/or rises above the system pressure limit 158 and giving the user an option to override and/or ignore the system pressure limit 158, thereby returning the controller 48 to the flow control mode 140 and permitting the measured system pressure 152 to continue to rise above and/or remain above the system pressure limit 158. The controller 48 may be configured to automatically switch from the flow control mode 140 to the system pressure override mode 150 unless the user has expressly acknowledged the option to override and/or ignore the system pressure limit 158 and/or expressly directed the controller 48 to return to the flow control mode 140.

In some embodiments, when the measured pressure (e.g., system pressure 152) is relieved and/or falls below the preset pressure threshold (e.g., the system pressure limit 158), as shown at reference 156, the controller 48 may be configured to switch from the system pressure override mode 150 back to the flow control mode 140. In some embodiments, the controller 48 may be configured to display a prompt of the display 44 asking if the user wants to switch out of the system pressure override mode 150 when the measured pressure is relieved and/or falls below the preset pressure threshold. In some embodiments, the prompt may ask if the user wants to switch from the system pressure override mode 150 back to the flow control mode 140 or to an adjusted flow control mode 141. In at least some embodiments, when switching back to the flow control mode 140, the flow rate may return to the target flow rate 142 configured by and/or associated with the flow control mode 140, as shown at reference 146 in FIG. 9. In some embodiments, the controller 48 may be configured to display a prompt on the display 44 asking if the user wants to switch back to the flow control mode 140 when the measured pressure (e.g., system pressure 152) falls below the preset pressure threshold. In some embodiments, the controller 48 may be configured to display a notification on the display 44 and automatically switch from the system pressure override mode 150 back to the flow control mode 140 when the measured pressure (e.g., system pressure 152) falls below the preset pressure threshold.

In some embodiments, when the measured pressure (e.g., system pressure 152) is relieved and/or falls below the preset pressure threshold (e.g., the system pressure limit 158), as shown at reference 156, the controller 48 may be configured to switch from the system pressure override mode 150 to the adjusted flow control mode 141. The controller 48 may be configured to operate at the reduced flow rate of the system pressure override mode 150 when in the adjusted flow control mode 141, as shown at reference 148 in FIG. 10. For example, in the adjusted flow control mode 141, the flow rate may be thereafter maintained at the reduced flow rate associated with the system pressure override mode 150. In some embodiments, the controller 48 may be configured to display a prompt on the display 44 asking if the user wants to switch to the adjusted flow control mode 141 when the measured pressure (e.g., system pressure 152) falls below the preset pressure threshold. In some embodiments, the controller 48 may be configured to display a notification on the display 44 and automatically switch from the system pressure override mode 150 to the adjusted flow control mode 141 when the measured pressure (e.g., system pressure 152) falls below the preset pressure threshold.

Figure 11:
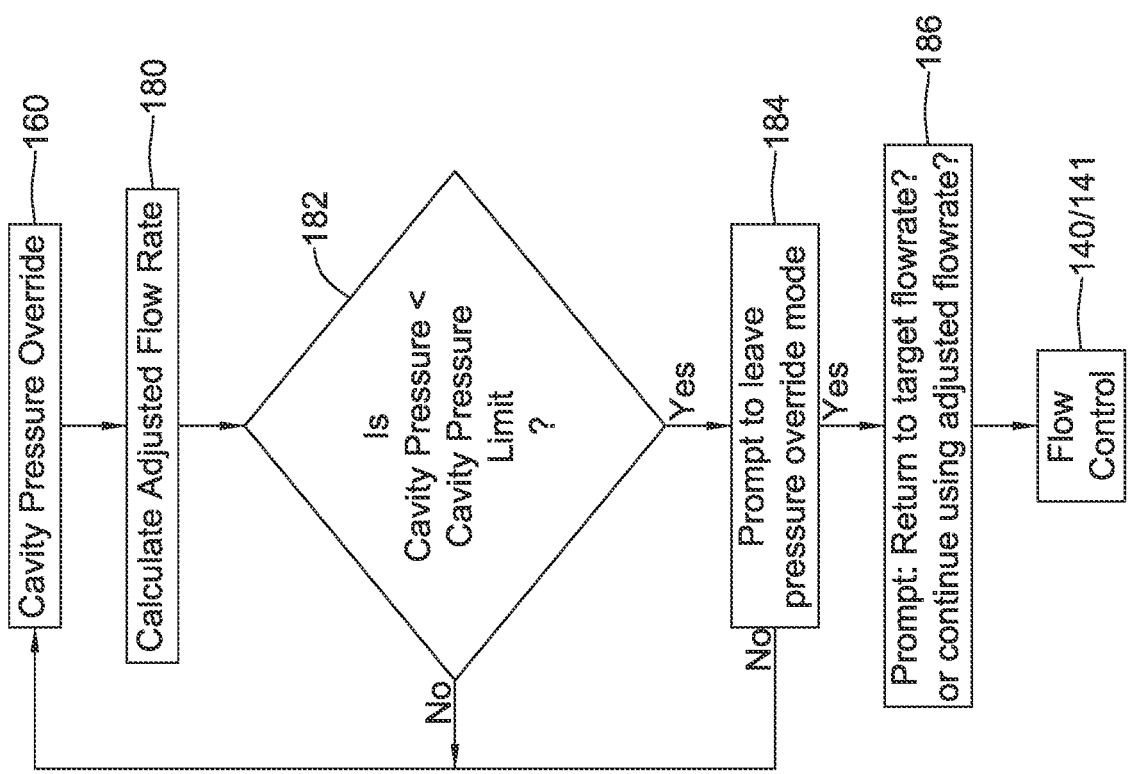
FIG. 11 is a flow chart illustrating aspects of a cavity pressure override mode of the fluid management system.

FIG. 11 is a flow chart illustrating aspects of the cavity pressure override mode 160. When the controller 48 switches to the cavity pressure override mode 160 as discussed herein, the controller 48 may be configured to calculate an adjusted flow rate or a reduced flow rate that depends on the target flow rate 142, the actual flow rate, and/or the measured intracavity pressure 162 relative to the preset pressure threshold (e.g., the intracavity pressure limit 168), as shown at reference 180. Next, the controller 48 may compare the measured pressure (e.g., the intracavity pressure 162) plus a preset tolerance (e.g., 5%, 10%, 15%, 25%, etc.) to the intracavity pressure limit 168 set at reference 104, as seen at reference 182. In some embodiments, if the measured intracavity pressure 162 plus the preset tolerance is greater than (e.g., exceeds) the intracavity pressure limit 168 set at reference 104, the controller 48 may proceed to compare the system pressure to the system pressure limit set as discussed herein. In some embodiments, if the measured intracavity pressure 162 plus the preset tolerance is greater than the intracavity pressure limit 168 set at reference 104, the controller 48 may proceed to operate at the reduced flow rate to return the measured intracavity pressure 162 at or below the intracavity pressure limit 168 while continuing to monitor the measured intracavity pressure 162 in the cavity pressure override mode 160. The controller 48 may then proceed to begin the queries again.

In some embodiments, if the measured intracavity pressure 162 plus the preset tolerance is less than the intracavity pressure limit 168 set at reference 104, the controller 48 may be configured to display a prompt on the display 44 asking if the user wants to switch out of (e.g., leave) the cavity pressure override mode 160, as seen at reference 184. If the user responds with a "no", or in some embodiments fails to respond at all, the controller 48 may continue to operate at the reduced flow rate while continuing to monitor the measured intracavity pressure 162 in the cavity pressure override mode 160. The controller 48 may then proceed to begin the queries again. If the user responds with a "yes", the controller 48 may then display a second prompt on the display 44 asking if the user wants to return to the flow control mode 140 using the target flow rate 142 or if the user wants to switch to the adjusted flow control mode 141 by continuing to use the reduced flow rate, as shown at reference 186. The controller 48 may then proceed to operate in the flow control mode 140 or the adjusted flow control mode 141 according to the user selection.

Figure 12:
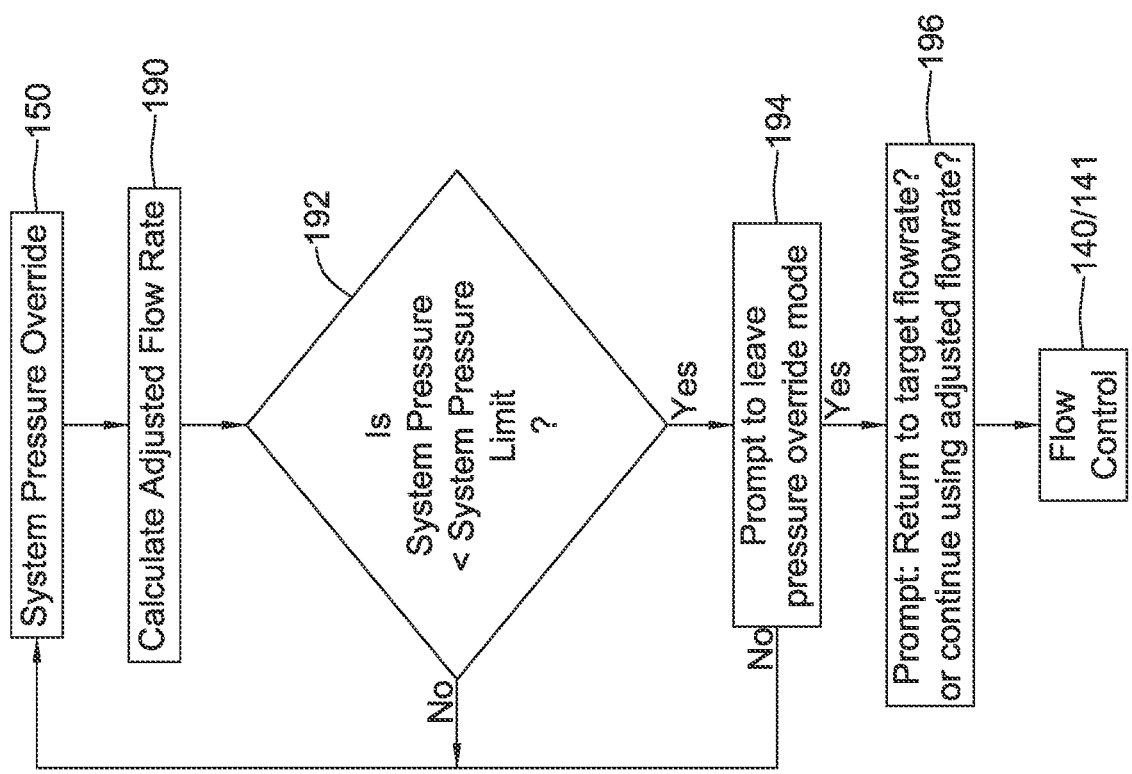
FIG. 12 is a flow chart illustrating aspects of a system pressure override mode of the fluid management system.

FIG. 12 is a flow chart illustrating aspects of the system pressure override mode 150. When the controller 48 switches to the system pressure override mode 150 as discussed herein, the controller 48 may be configured to calculate an adjusted flow rate or a reduced flow rate that depends on the target flow rate 142, the actual flow rate, and/or the measured system pressure 152 relative to the preset pressure threshold (e.g., the system pressure limit 158), as shown at reference 190. Next, the controller 48 may compare the measured pressure (e.g., the system pressure 152) plus a preset tolerance (e.g., 5%, 10%, 15%, 25%, etc.) to the system pressure limit 158 set at reference 104/106, as seen at reference 192. In some embodiments, if the measured system pressure 152 plus the preset tolerance is greater than (e.g., exceeds) the system pressure limit 158 set at reference 104/106, the controller 48 may proceed to operate at the reduced flow rate to return the measured system pressure 152 at or below the system pressure limit 158 while continuing to monitor the measured system pressure 152 in the system pressure override mode 150. The controller 48 may then proceed to begin the queries again.

In some embodiments, if the measured system pressure 152 plus the preset tolerance is less than the system pressure limit 158 set at reference 104/106, the controller 48 may be configured to display a prompt on the display 44 asking if the user wants to switch out of (e.g., leave) the system pressure override mode 150, as seen at reference 194. If the user responds with a "no", or in some embodiments fails to respond at all, the controller 48 may continue to operate at the reduced flow rate while continuing to monitor the measured system pressure 152 in the system pressure override mode 150. The controller 48 may then proceed to begin the queries again. If the user responds with a "yes", the controller 48 may then display a second prompt on the display 44 asking if the user wants to return to the flow control mode 140 using the target flow rate 142 or if the user wants to switch to the adjusted flow control mode 141 by continuing to use the reduced flow rate, as shown at reference 196. The controller 48 may then proceed to operate in the flow control mode 140 or the adjusted flow control mode 141 according to the user selection.

In some embodiments, a method of controlling fluid flow in a fluid management system 10, wherein the fluid management system comprises an inflow pump 50 configured to pump fluid from a fluid supply source 34 to a treatment site within a patient at a flow rate and a controller 48 configured to operate at a target flow rate 142 in a flow control mode 140, may comprise setting parameters within the controller 48, wherein the parameters include the target flow rate 142 and a preset pressure threshold. In some embodiments, the preset pressure threshold is the intracavity pressure limit 168. In some embodiments, the preset pressure threshold is the system pressure limit 158.

In some embodiments, the method may comprise operating the controller 48 in the flow control mode 140, wherein the controller 48 maintains the target flow rate 142 while monitoring a measured pressure communicated to the controller 48 from a pressure sensor. In some embodiments, the measured pressure may be the intracavity pressure 162. In some embodiments, the intracavity pressure 162 may be communicated to the controller 48 from the pressure sensor 74. Other configurations are also contemplated. In some embodiments, the measured pressure may be the system pressure 152. In some embodiments, the system pressure 152 may be communicated to the controller 48 from the pressure sensor 67. Other configurations are also contemplated.

In some embodiments, the method may comprise a step of when the measured pressure reaches the preset pressure threshold, automatically switching the controller 48 from the flow control mode 140 to a pressure override mode in which the controller 48 automatically reduces the flow rate below the target flow rate 142 to return the measured pressure at or below the preset pressure threshold. In some embodiments, the method may include automatically switching the controller 48 from the flow control mode 140 to a cavity pressure override mode 160 in which the controller 48 automatically reduces the flow rate below the target flow rate 142 to return the measured intracavity pressure 162 at or below the intracavity pressure limit 168. In some embodiments, the controller 48 may be configured to display a notification on the display 44 informing the user that the controller 48 has switched from the flow control mode 140 to the cavity pressure override mode 160 when the measured intracavity pressure 162 reaches and/or rises above the intracavity pressure limit 168. In some embodiments, the controller 48 may be configured to display a prompt on the display 44 informing the user that the controller 48 has switched from the flow control mode 140 to the cavity pressure override mode 160 when the measured intracavity pressure 162 reaches and/or rises above the intracavity pressure limit 168 and giving the user an option to override and/or ignore the intracavity pressure limit 168, thereby returning the controller 48 to the flow control mode 140 and permitting the measured intracavity pressure 162 to continue to rise above and/or remain above the intracavity pressure limit 168. The controller 48 may be configured to automatically switch from the flow control mode 140 to the cavity pressure override mode 160 unless the user has expressly acknowledged the option to override and/or ignore the intracavity pressure limit 168 and/or expressly directed the controller 48 to return to the flow control mode 140.

In some embodiments, the method may include automatically switching the controller 48 from the flow control mode 140 to a system pressure override mode 150 in which the controller 48 automatically reduces the flow rate below the target flow rate 142 to return the measured system pressure 152 at or below the system pressure limit 158. In some embodiments, the controller 48 may be configured to display a notification on the display 44 informing the user that the controller 48 has switched from the flow control mode 140 to the system pressure override mode 150 when the measured system pressure 152 reaches and/or rises above the system pressure limit 158. In some embodiments, the controller 48 may be configured to display a prompt on the display 44 informing the user that the controller 48 has switched from the flow control mode 140 to the system pressure override mode 150 when the measured system pressure 152 reaches and/or rises above the system pressure limit 158 and giving the user an option to override and/or ignore the system pressure limit 158, thereby returning the controller 48 to the flow control mode 140 and permitting the measured system pressure 152 to continue to rise above and/or remain above the system pressure limit 158. The controller 48 may be configured to automatically switch from the flow control mode 140 to the system pressure override mode 150 unless the user has expressly acknowledged the option to override and/or ignore the system pressure limit 158 and/or expressly directed the controller 48 to return to the flow control mode 140.

In some embodiments, the method may comprise displaying a prompt on the display 44 asking if the user wants to switch out of the pressure override mode (e.g., the cavity pressure override mode 160 and/or the system pressure override mode 150) when the measured pressure (e.g., the intracavity pressure 162 and/or the system pressure 152, respectively) falls below the preset pressure threshold (e.g., the intracavity pressure limit 168 and/or the system pressure limit 158, respectively). In some embodiments, the method may comprise at such time as the measured pressure falls below the preset pressure threshold, displaying the prompt of the display 44 asking if the user wants to switch out of the pressure override mode. As such, in at least some embodiments, displaying the prompt is correlated to the timing of the measured pressure falling below the preset pressure threshold.

In some embodiments, the method may further include, if the user confirms switching out of the pressure override mode, displaying a prompt on the display 44 asking if the user wants to return to the flow control mode 140 and the target flow rate 142 or if the user wants to switch to the adjusted flow control mode 141 and continue using the reduced flow rate associated with the pressure override mode (e.g., the cavity pressure override mode 160 and/or the system pressure override mode 150).

In some embodiments, the intracavity pressure limit 168 and/or the system pressure limit 158 may be in a range from −600 mmHg to +600 mmHg, from −300 mmHg to +300 mmHg, from 0 mmHg to +300 mmHg, from +25 mmHg to +250 mmHg, from +50 mmHg to +150 mmHg, or another suitable range. In some embodiments, the intracavity pressure limit 168 and/or the system pressure limit 158 may be selected and/or determined at least in part based on the capabilities of the pressure sensor 67 and/or the pressure sensor 74. In some embodiments, the preset tolerance for the intracavity pressure limit 168 and/or the system pressure limit 158 may be +/−5%, +/−10%, +/−15%, +/−20%, +/−25%, +/−30%, or another suitable range or value. In some embodiments, the preset tolerance for the intracavity pressure limit 168 and/or the system pressure limit 158 may be +/−2 mmHg, +/−5 mmHg, +/−10 mmHg, +/−15 mmHg, or another range.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

The materials that can be used for the various components of the system(s) and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the fluid management system, the medical device, the elongate shaft, the inflow pump, the fluid warming system, the controller, the supply line(s), the load cells, the handle, the workstation, the display screen(s), the fluid supply source(s), the collection container(s), and/or elements or components thereof.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL®

400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof, or any other suitable material.

In at least some embodiments, portions or all of the system, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system, and/or components or portions thereof, may be made of a material that does not substantially distort the image and create substantial artifacts (i.e., gaps in the image). Certain ferromagnetic materials, for example, may not be suitable because they may create artifacts in an MRI image. The system, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A fluid management system, comprising:
   an inflow pump configured to pump fluid from a fluid supply source to a treatment site within a patient at a flow rate; and
   a controller configured to operate at a target flow rate in a flow control mode;
   wherein in the flow control mode, the controller is configured to maintain the target flow rate while monitoring a measured pressure communicated to the controller from a pressure sensor;
   wherein when the measured pressure reaches a preset pressure threshold, the controller is configured to automatically switch from the flow control mode to a pressure override mode in which the controller automatically reduces the flow rate below the target flow rate while still pumping fluid to the treatment site to return the measured pressure at or below the preset pressure threshold.

2. The fluid management system of claim 1, wherein the controller is configured to switch from the pressure override mode back to the flow control mode when the measured pressure falls below the preset pressure threshold.

3. The fluid management system of claim 2, wherein the controller is configured to display a prompt on a display asking if a user wants to switch back to the flow control mode when the measured pressure falls below the preset pressure threshold.

4. The fluid management system of claim 2, wherein the controller is configured to display a notification on a display and automatically switch from the pressure override mode back to the flow control mode when the measured pressure falls below the preset pressure threshold.

5. The fluid management system of claim 1, wherein the controller is configured to switch from the pressure override mode to an adjusted flow control mode when the measured pressure falls below the preset pressure threshold.

6. The fluid management system of claim 5, wherein the controller is configured to operate at the reduced flow rate of the pressure override mode when in the adjusted flow control mode.

7. The fluid management system of claim 5, wherein the controller is configured to display a prompt on a display asking if a user wants to switch to the adjusted flow control mode when the measured pressure falls below the preset pressure threshold.

8. The fluid management system of claim 5, wherein the controller is configured to display a notification on a display and automatically switch from the pressure override mode to the adjusted flow control mode when the measured pressure falls below the preset pressure threshold.

9. The fluid management system of claim 1, wherein the measured pressure is an intracavity pressure measured within the treatment site.

10. The fluid management system of claim 9, wherein the preset pressure threshold is an intracavity pressure limit.

11. The fluid management system of claim 1, wherein the measured pressure is a system pressure measured within the fluid management system.

12. The fluid management system of claim 11, wherein the preset pressure threshold is a system pressure limit.

13. A fluid management system, comprising:
- an inflow pump configured to pump fluid from a fluid supply source to a treatment site within a patient at a flow rate; and
- a controller configured to operate at a target flow rate in a flow control mode;
- wherein in the flow control mode, the controller is configured to maintain the target flow rate while monitoring a measured pressure communicated to the controller from a pressure sensor;
- wherein when the measured pressure reaches a preset pressure threshold, the controller is configured to automatically switch from the flow control mode to a pressure override mode in which the controller automatically reduces the flow rate below the target flow rate while still pumping fluid to the treatment site to return the measured pressure at or below the preset pressure threshold;
- wherein the controller is configured to display a prompt on a display asking if a user wants to switch out of the pressure override mode when the measured pressure falls below the preset pressure threshold.

14. The fluid management system of claim 13, wherein the controller is configured to switch from the pressure override mode back to the flow control mode when the measured pressure falls below the preset pressure threshold.

15. The fluid management system of claim 13, wherein the controller is configured to switch from the pressure override mode to an adjusted flow control mode when the measured pressure falls below the preset pressure threshold.

16. The fluid management system of claim 15, wherein in the adjusted flow control mode, the flow rate is thereafter maintained at the reduced flow rate associated with the pressure override mode.

17. The fluid management system of claim 13, wherein the prompt asks if the user wants to switch back to the flow control mode or to an adjusted flow control mode.

18. A method of controlling fluid flow in a fluid management system, wherein the fluid management system comprises an inflow pump configured to pump fluid from a fluid supply source to a treatment site within a patient at a flow rate and a controller configured to operate at a target flow rate in a flow control mode, the method comprising:
- setting parameters within the controller, wherein the parameters include the target flow rate and a preset pressure threshold;
- operating the controller in the flow control mode, wherein the controller maintains the target flow rate while monitoring a measured pressure communicated to the controller from a pressure sensor;
- when the measured pressure reaches the preset pressure threshold, automatically switching the controller from the flow control mode to a pressure override mode in which the controller automatically reduces the flow rate below the target flow rate while still pumping fluid to the treatment site to return the measured pressure at or below the preset pressure threshold; and
- displaying a prompt on a display asking if a user wants to switch out of the pressure override mode when the measured pressure falls below the preset pressure threshold.

19. The method of claim 18, wherein the preset pressure threshold is an intracavity pressure limit.

20. The method of claim 18, wherein the preset pressure threshold is a system pressure limit.

\* \* \* \* \*